United States Patent
Givens et al.

(10) Patent No.: US 10,368,785 B2
(45) Date of Patent: Aug. 6, 2019

(54) IN-EAR HEARING TEST PROBE DEVICES AND METHODS AND SYSTEMS USING SAME

(71) Applicant: East Carolina University, Greenville, NC (US)

(72) Inventors: Gregg D. Givens, Greenville, NC (US); Jianchu Yao, Winterville, NC (US)

(73) Assignee: East Carolina University, Greenville, NC (US)

( * ) Notice: Subject to any disclaimer, the term of this patent is extended or adjusted under 35 U.S.C. 154(b) by 0 days.

(21) Appl. No.: 15/812,443

(22) Filed: Nov. 14, 2017

(65) Prior Publication Data

US 2018/0064374 A1 Mar. 8, 2018

Related U.S. Application Data

(63) Continuation-in-part of application No. 13/124,280, filed as application No. PCT/US2009/005789 on Oct. 23, 2009.

(Continued)

(51) Int. Cl.
*G06Q 50/22* (2018.01)
*G16H 40/63* (2018.01)
(Continued)

(52) U.S. Cl.
CPC ............ *A61B 5/121* (2013.01); *A61B 5/0022* (2013.01); *A61B 5/72* (2013.01); *A61B 5/7465* (2013.01);
(Continued)

(58) Field of Classification Search
CPC ........ G06Q 10/00; G06Q 50/00; G16H 10/00; G16H 15/00; G16H 20/00; G16H 30/00;
(Continued)

(56) References Cited

U.S. PATENT DOCUMENTS 3,392,241 A 7/1968 Weiss et al.
3,536,835 A 10/1970 Rawls et al.
(Continued)

FOREIGN PATENT DOCUMENTS

EP 1769412 4/2007
WO WO98/02083 1/1998
(Continued)

OTHER PUBLICATIONS

Office Action for corresponding Canadian Application 2,741,201, dated Nov. 2, 2017, 5 pages.
(Continued)

*Primary Examiner* — Robert W Morgan
*Assistant Examiner* — Charles P Coleman
(74) *Attorney, Agent, or Firm* — Myers Bigel, P.A.

(57) ABSTRACT

A medical hearing testing method includes: inserting an in-ear test probe that is coupled to a hearing test adapter into an ear of a patient at a patient site; receiving device identification data at a web portal operating on a first electronic device over an electronic network between the first electronic device and the hearing test adapter, wherein the device identification data is uniquely identifies the hearing test adapter; receiving a control operation associated with a test session from the first user at the web portal; and responsive to receiving the control operation, transmitting an operational command from the web portal to the hearing test adapter over the electronic network, wherein the operational command controls an operation of the test probe.

29 Claims, 17 Drawing Sheets

Related U.S. Application Data

(60) Provisional application No. 61/108,116, filed on Oct. 24, 2008.

(51) Int. Cl.
  *G16H 40/67* (2018.01)
  *G16H 10/60* (2018.01)
  *A61B 5/12* (2006.01)
  *A61B 5/00* (2006.01)
  *G06F 19/00* (2018.01)

(52) U.S. Cl.
  CPC ......... *G06F 19/3418* (2013.01); *G06Q 50/22* (2013.01); *G16H 10/60* (2018.01); *G16H 40/63* (2018.01); *G16H 40/67* (2018.01)

(58) Field of Classification Search
  CPC ........ G16H 40/00; G16H 50/00; G16H 70/00; G16H 80/00; G16H 10/40; G16H 20/10; G16H 20/13; G16H 20/17
  USPC .................................................. 705/2, 3, 20
  See application file for complete search history.

(56) References Cited

U.S. PATENT DOCUMENTS

| | | |
|---|---|---|
| 3,793,484 A | 2/1974 | Feezor |
| 3,793,485 A | 2/1974 | Feezor et al. |
| 3,799,146 A | 3/1974 | John et al. |
| 3,808,354 A | 4/1974 | Feezor et al. |
| 3,974,335 A | 8/1976 | Blackledge |
| 4,002,161 A | 1/1977 | Klar et al. |
| 4,009,707 A | 3/1977 | Ward |
| 4,024,499 A | 5/1977 | Bosscher |
| 4,038,496 A | 7/1977 | Feezor |
| 4,201,225 A | 5/1980 | Bethea, III et al. |
| 4,275,744 A | 6/1981 | Thornton et al. |
| 4,284,847 A | 8/1981 | Besserman |
| 4,374,526 A | 2/1983 | Kemp |
| 4,388,595 A | 6/1983 | Brooks |
| 4,489,610 A | 12/1984 | Slavin |
| 4,556,069 A | 12/1985 | Dalton, Jr. et al. |
| 4,601,295 A | 7/1986 | Teele |
| 4,688,582 A | 8/1987 | Heller et al. |
| 4,759,070 A | 7/1988 | Voroba et al. |
| 4,768,165 A | 8/1988 | Hohn |
| 4,847,763 A | 7/1989 | Moser et al. |
| 4,884,447 A | 12/1989 | Kemp et al. |
| 4,961,895 A | 10/1990 | Klein |
| 5,105,822 A | 4/1992 | Stevens et al. |
| 5,197,332 A | 3/1993 | Shennib |
| 5,216,425 A | 6/1993 | Erhage |
| 5,303,327 A | 4/1994 | Sturner et al. |
| 5,372,142 A | 12/1994 | Madsen et al. |
| 5,402,493 A | 3/1995 | Goldstein |
| 5,419,312 A | 5/1995 | Arenberg et al. |
| 5,421,818 A | 6/1995 | Arenberg |
| 5,428,998 A | 7/1995 | Downs |
| 5,441,047 A | 8/1995 | David et al. |
| 5,473,460 A | 12/1995 | Haner et al. |
| 5,474,529 A | 12/1995 | Arenberg |
| 5,476,446 A | 12/1995 | Arenburg |
| 5,526,819 A | 6/1996 | Lonsbury-Martin et al. |
| 5,546,956 A | 8/1996 | Thornton |
| 5,594,174 A | 1/1997 | Keefe |
| 5,628,330 A | 5/1997 | Upham |
| 5,651,371 A | 7/1997 | Keefe |
| 5,664,577 A | 9/1997 | Lansbury-Martin et al. |
| 5,687,717 A | 11/1997 | Halpern et al. |
| 5,697,379 A | 12/1997 | Neely et al. |
| 5,699,809 A | 12/1997 | Combs et al. |
| 5,734,827 A | 3/1998 | Thornton et al. |
| 5,755,230 A | 5/1998 | Schmidt et al. |
| 5,776,144 A | 7/1998 | Leysieffer et al. |
| 5,776,179 A | 7/1998 | Ren et al. |
| 5,792,072 A | 8/1998 | Keefe |
| 5,792,073 A | 8/1998 | Keefe |
| 5,811,681 A | 9/1998 | Braun et al. |
| 5,825,894 A | 10/1998 | Shennib |
| 5,868,682 A | 2/1999 | Combs et al. |
| 5,885,225 A | 3/1999 | Keefe et al. |
| 5,917,375 A | 6/1999 | Lisco et al. |
| 5,928,160 A | 7/1999 | Clark et al. |
| 5,954,667 A | 9/1999 | Finkenzeller et al. |
| 6,033,076 A | 3/2000 | Bracuning et al. |
| 6,051,849 A | 4/2000 | Davis et al. |
| 6,071,246 A | 6/2000 | Stürzebecher et al. |
| 6,083,156 A | 7/2000 | Lisiecki |
| 6,086,541 A | 7/2000 | Rho |
| 6,110,126 A | 8/2000 | Zoth et al. |
| 6,171,237 B1 | 1/2001 | Avitall et al. |
| 6,283,761 B1 | 9/2001 | Joao |
| 6,319,207 B1 | 11/2001 | Naidoo |
| 6,322,521 B1 | 11/2001 | Hou |
| 6,350,243 B1 | 2/2002 | Johnson |
| 6,366,863 B1 | 4/2002 | Bye et al. |
| 6,379,314 B1 | 4/2002 | Horn |
| 6,428,485 B1 | 8/2002 | Rho |
| 6,468,224 B1 | 10/2002 | Foreman et al. |
| 6,513,060 B1 | 1/2003 | Nixon et al. |
| 6,535,878 B1 | 3/2003 | Guedalia et al. |
| 6,647,345 B2 | 11/2003 | Bye et al. |
| 6,882,732 B2 | 4/2005 | Pavlakos |
| 6,916,291 B2 | 7/2005 | Givens et al. |
| 6,917,373 B2 | 7/2005 | Vong et al. |
| 6,964,642 B2 | 11/2005 | Wasden et al. |
| 6,974,421 B1 | 12/2005 | Causevic et al. |
| 7,016,504 B1 | 3/2006 | Shennib |
| 7,370,533 B2 | 5/2008 | Davis |
| 7,530,957 B2 | 5/2009 | Givens et al. |
| 7,996,212 B2 | 8/2011 | Klefenz |
| 2001/0027335 A1 | 10/2001 | Meyerson et al. |
| 2002/0049684 A1 | 4/2002 | Nagamoto et al. |
| 2002/0076056 A1 | 6/2002 | Pavlakos |
| 2002/0124100 A1 | 9/2002 | Adams |
| 2002/0165466 A1* | 11/2002 | Givens .................. A61B 5/121 600/559 |
| 2005/0085343 A1 | 4/2005 | Burrows et al. |
| 2005/0192515 A1* | 9/2005 | Givens .................. A61B 5/121 600/559 |
| 2005/0026778 A1 | 12/2005 | Kazman |
| 2005/0267778 A1* | 12/2005 | Kazman ................. G06Q 10/00 705/26.1 |
| 2006/0122870 A1* | 6/2006 | Austin .................. G06F 19/322 705/3 |
| 2007/0027714 A1* | 2/2007 | Fenno ................... G06F 19/327 705/2 |
| 2007/0273504 A1* | 11/2007 | Tran ..................... A61B 5/0022 340/539.12 |
| 2008/0004904 A1* | 1/2008 | Tran ..................... A61B 5/0006 705/2 |
| 2008/0165980 A1* | 7/2008 | Pavlovic ............... H03G 9/005 381/60 |
| 2008/0194984 A1* | 8/2008 | Keefe .................... A61B 5/121 600/559 |
| 2009/0062687 A1 | 3/2009 | Givens et al. |
| 2009/0164917 A1 | 6/2009 | Kelley |
| 2011/0060244 A1 | 3/2011 | Givens et al. |
| 2011/0257994 A1* | 10/2011 | Givens ................ G06F 19/3418 705/2 |
| 2013/0006140 A1 | 1/2013 | Givens et al. |

FOREIGN PATENT DOCUMENTS

| | | |
|---|---|---|
| WO | WO99/04043 | 1/1999 |
| WO | WO01/06916 | 2/2001 |
| WO | WO2006/032101 | 3/2003 |

(56) References Cited

FOREIGN PATENT DOCUMENTS

| WO | 2007000231 | 1/2007 |
|---|---|---|
| WO | WO10/05789 | 1/2010 |

OTHER PUBLICATIONS

Frank, Ansi Update: Specification of Audiometers, Nov. 1997, American Journal of Audiology, vol. 6, No. 3, pp. 29-32.
*Hearing Screening with the OtoScreen I, General Information*: http://www.handtronix.com/HTX/OTOInfo.html, 3 pages, (printed Sep. 6, 2000).
*What's new in hearing screening and audiology*, http://www.handtronix.com, 4 pages (date of publication Feb. 2001), (printed Apr. 19, 2002).
*Our Portable Audiometry Solutions*, Otovation, http://www.otovation.com/solutions.html, 2 pages, © 2004-2008, printed from website May 30, 2008.
Alsarraf et al., *Otitis Media Health Status Evaluation: A Pilot Study for the Investigation of Cost-Effective Outcomes of Recurrent Acute Otitis Media Treatment*, Annals of Otology, Rhinology and Laryngology 107(2): 120-128, (1998).
Alusi et al., *Tele-education: the virtual medical laboratory*, J Telemed Telecare 3(Suppl 1): 79-81, Abstract Only, 1 page, (1997).
American Academy of Pediatrics, *Newborn and Infant Hearing Loss: Detection and Intervention*, Pediatrics 103(2): 527-530, (1999).
Anonymous: "User Groups and Access Permissions", In: "E-Quals Level 2 IT principles", Jan. 1, 2003, 1 page.
Bess et al., *Children with Minimal Sensorineural Hearing Loss: Prevalence, Educational Performance and Functional Status*, Ear and Hearing 19 (5): 339-354, (1998).
Blakeslee et al., *Practice of otolaryngology via telemedicine*, Laryngoscope 108(1) Pt 1:1-7, Abstract Only, 1 sheet, (Jan. 1998).
Burgess et al., *Abstract of Overview of telemedicine applications for otolaryngology*, Jnl Laryngoscope, 109(9): 1433-1437, (Sep. 1999).
Carrell et al., *Letter to the Editor Interactive Software for Evaluating Auditory Discrimination*, Ear & Hearing, pp. 175-176, (1999).
Collins, J., *Prevalence of Selected Chronic Conditions*, U.S. 1990-1992, Natl Center for Health Statistics, Vital Health Statistics, 10(194): iii-8, (1997).
Crump et al., *A field trial of the NASA Telemedicine Instrument Pack in a family practice*, Aviat Space Environ Med 67(11): 1080-1085, Abstract Only, 1 page, (Nov. 1996).
Extended European Search Report for corresponding EP application No. 09 82 2340, dated Jul. 18, 2017, 13 pages.
Finitzo et al.., *The Newborn with Hearing Loss: Detection in the Nursery*, Pediatrics (102): 1452-1460, (1998).
Freid et al., *Ambulatory Health Care Visits by Children: Principal Diagnosis and Place of Visit*, Natl Center for Health Statistics, Vital and Health Statistics 13(137): 17, iii-23, (1998).
Furukawa et al., *Telemedicine in laryngology*, Jibi Inkoka Tokeibu Geka 70(12): 855-856, Abstract Only, 1 page, (1998).
Givens et al., *Internet Application to Tele-Audiology-"Nothin' but Net"*, Journal of Speech, Language, and Hearing Research, vol. 12 (2): 59-65, (Dec. 2003).
Givens et al., *Internet Based Tele-Audiometry System for the Assessment of Hearing: A Pilot Study*, Telemedicine Journal and e-Health, vol. 9 (4): 375-378, (2003).
Gorlin et al., *Hereditary Hearing Loss and Its Syndromes*, New York: Oxford University Press, p. xv-xxxiii, (1995).
Hall, J. W., *Handbook of Otoacoustic Emissions*, Singular Publishing Group, pp. 20 and 24 (1999).
Heneghan et al., *Telemedicine applications in otolaryngology*, IEEE Eng Med Biol Mag 18(4): 53-62, Abstract Only, 2 pages, (Jul.-Aug. 1999).
Holtan, Amy, *Patient reactions to specialist telemedicine consultations—a sociological approach*, J. Telemed Telecare 4: 206-213, (1998).
Hutchinson, J. R., *Telemedicine in otolaryngology*, Otolaryngol Clin North Am, 31(2): 319-329, Abstract, 1 page, (Apr. 1998).
International Search Report and Written Opinion for PCT application No. PCT/US09/48520, dated Aug. 7, 2009.
International Search Report for PCT/US09/005789, dated May 24, 2010.
Joint Committee on Infant Hearing Screening, 1994 Position Statement, American Speech-Language-Hearing Assn. 36(12), 11 pages, (Dec. 1994).
Kelly, L., *Using Silent Motion Pictures to Teach Complex Syntax to Adult Deaf Readers*, Journal of Deaf Studies and Deaf Education 3: 217-230, Abstract Only, 1 page, (1998).
Krumm, Mark, "Audiology telemedicine", Journal of Telemedicine and Telecare, vol. 13, No. 5, Jul. 1, 2007, pp. 224-229.
Made et al., *Tele-otolaryngology consultations between two rural primary-care centres in southern Lapland and the University Hospital of Umeå*, J. Telemed Telecare 5, Suppl 1, S1:93-S1:94, (1999).
Martin, F.N., *A Study Guide Introduction to Audiology*, $2^{nd}$ Edition, University of Texas, 2 pages, (1991).
Masterson et al., *New & Emerging Technologies. Going Where We've Never Gone Before*, ASHA 41(3): 16-20 (May-Jun. 1999).
Morton, N.E., *Genetic Epidemiology of Hearing Impairment*, Annals of the New York Academy of Sciences 630: 16-31, (1991).
Natl Institute on Deafness and Other Communication Disorders, *Natl Strategic Research Plan: Hearing and Hearing Impairment*, Bethesda, Md, U.S. Dept. of Health and Human Services, Natl Institutes of Health, pp. ii-110, (1996).
Niskar et al., *Prevalence of Hearing Loss Among Children 6 to 19 Years of Age, The Third Natl Health and Nutrition Examination Survey*, Journal of the American Medical Assn. 279(14): 1071-1075, Abstract Only, 2 pages, (1998).
Office Action for corresponding Canadian Application No. 2,741,201, dated Dec. 13, 2016, 6 pages.
Schappert, *Office Visits for Otitis Media: United States, 1975-1990*, Advance Data 214: 1-20, (1992).
Steinberg, A., *Issues in Providing Mental Health Services to Hearing Impaired Persons*, Hospital & Community Psychiatry 42(4): 380-389, (1991).
Stern et al., *Telemedicine applications in otolaryngology*, Journal of Telemed Telecare 4 (Suppl 1): 74-75, (1998).
Straub, K., *Health care videoconferencing options cover wide range of applications, prices, quality*, Health Mgmt Tech 18(5): 52-3, 55-6, Abstract Only, 1 page, (Apr. 1997).
Wolbransky et al., *ATA Conference Report. Telemedicine in the new millennium*, MD Computing 16(4): 40-43, (Jul.-Aug. 1999).
Yao, Jianchu et al., *A Tele-Hearing Diagnosis System Based on Web Services*, American Telemedicine Association 2009 Concurrent Poster Presentation Abstracts, four pages,181, Apr. 2009.
Yao et al., A Web Services-Based Distributed System with Browser-Client Architecture to Promote Tele-audiology Assessment, Telemedicine and e-Health, Oct. 2009, pp. 777-782, vol. 15, No. 8.
Yao et at, Using Web Services to Realize Remote Hearing Assessment, Journal of Clinical Monitoring and Computing, 2010, pp. 41-50, vol. 24.
Yoo et al, *Cochlear Modeling and Visualization on the Internet*, Int'l Congress Series No. 1191:1044-1045, (1999).
Yoshinaga-Itano et al., *Identification of Hearing Loss after age 18 Months is not Early Enough*, American Annals of the Deaf 143(5): 380-387, (1998).
Yoshinaga-Itano et al., *Language of Early and Later-Identified Children with Hearing Loss*, Pediatrics 102(5): 1161-1171, (1998).
Wilson et al., *Eastern North Carolina Health Care Atlas, A resource for healthier communities*, pp. ii-II.B.46, (1997).
First Examination Report for corresponding Indian application No. 3424/CHENP/2011 dated Nov. 27, 2018, 4 pages.

\* cited by examiner

IN-EAR HEARING TEST PROBE DEVICES AND METHODS AND SYSTEMS USING SAME

RELATED APPLICATIONS

This application is a continuation-in-part of U.S. application Ser. No. 13/124,280, filed Jul. 7, 2011, which is a 35 U.S.C. § 371 national phase application of International Application No. PCT/US2009/005789, filed Oct. 23, 2009, which claims the benefit of and priority to U.S. Provisional Application Ser. No. 61/108,116, filed Oct. 24, 2008, the contents of which are hereby incorporated by reference as if recited in full herein.

A portion of the disclosure of this patent document contains material which is subject to copyright protection. The copyright owner, East Carolina University of Greenville, N.C., has no objection to the reproduction by anyone of the patent document or the patent disclosure, as it appears in the Patent and Trademark Office patent file or records, but otherwise reserves all copyright rights whatsoever.

FIELD OF THE INVENTION

The invention relates to hearing evaluation systems used to diagnose hearing impairments.

BACKGROUND

It is estimated that approximately 28 million people in the United States, including 1.46 million children, have a hearing deficiency in frequencies important to the understanding of speech. Early identification of hearing loss and appropriate intervention can be critical to preventing or ameliorating further hearing loss or language delay or disorder. Indeed, early identification can be particularly important in children who are, typically, more receptive to rehabilitation.

Conventional hearing evaluation or assessment tests are performed in a clinical setting with personal interaction between the patient and a clinician. In these settings, the patient is often required to sit in a sound isolation booth and to visually signal to the clinician when sounds generated from an audiometer become audible. Unfortunately, this clinic or office setting structure can be burdensome and time consuming, particularly for those individuals located in remote or rural regions for whom access to audiological specialists may be limited or the cost of transportation to a clinic or office may be unaffordable, or in industrial settings where frequent or periodical screenings may be beneficial.

U.S. Pat. No. 6,916,291 describes a diagnostic hearing system distributed via a computer network that allows interaction between an audiologist and a patient during a test session.

Despite the above, there remains a need for alternative Internet-based diagnostic hearing systems.

SUMMARY OF EMBODIMENTS OF THE INVENTION

Some embodiments of the invention are directed to a medical hearing testing method. The method includes: inserting an in-ear test probe that is coupled to a hearing test adapter into an ear of a patient at a patient site; electronically receiving device identification data at a web portal operating on a first electronic device over an electronic network between the first electronic device and the hearing test adapter, wherein the device identification data uniquely identifies the hearing test adapter; electronically receiving a first access request from a first user of the web portal, wherein the first access request requests a first session from among a plurality of sessions to perform a remote hearing test; electronically receiving a second access request from a second user of the web portal at the patient site; responsive to the second access request, electronically providing a second session and a second user interface, different from the first user interface, that is customized based on second access permissions for the second user over the web portal, wherein the second access permissions permit the second user to provide hearing test feedback responsive to the control of the hearing test adapter by the first user; connecting the first session and the second session into a test session based on geographic location and/or requested test times of the second user; modifying the first user interface to display test session data and device information corresponding to the device identification data received from the hearing test adapter; receiving a control operation associated with a test session from the first user at the web portal; and responsive to receiving the control operation, transmitting an operational command from the web portal to the hearing test adapter over the electronic network, wherein the operational command controls an operation of the test probe.

In some embodiments, the operational command controls the operation of the test probe to alter an internal pressure of the ear of the patient. Altering the internal pressure of the ear of the patient may include increasing a pressure of the ear canal with respect to an atmospheric pressure. Altering the internal pressure of the ear of the patient may include remotely electronically controlling operation of a manometer and/or a pump associated with the test probe. The operational command may control the operation of the test probe to output a tone using a speaker associated with the test probe during and/or after altering the internal pressure of the ear of the patient.

In some embodiments, the operational command controls the operation of the test probe to output a tone using a speaker associated with the test probe and to measure sound that reflects off a tympanic membrane of the patient's ear using a microphone associated with the test probe.

In some embodiments, the operational command is used to determine if the test probe is sealingly engaged with the patient's ear.

In some embodiments, the method includes: receiving a response to the operational command from the hearing test adapter over the electronic network at the web portal; and electronically storing the response in a storage medium coupled to the first electronic device. The response to the operational command may be a first response to a first operational command on a first date. The method may include: receiving a second response to a second operational command from the hearing test adapter over the electronic network at the web portal on a second date; and analyzing the first response and the second response from the second user to develop a hearing trend for the second user. The method may include altering a frequency of testing for the second user responsive to the determined hearing trend.

In some embodiments, the operational command controls the operation of the hearing test adapter and/or the test probe to alter the audio frequency of a tone transmitted by the test probe into the ear of the patient.

In some embodiments, the method includes transmitting multimedia communications between the first user and the second user over the electronic network during the test session, wherein transmitting multimedia communications comprises transmitting speech of the second during the test session.

Some other embodiments of the invention are directed to a medical hearing test method. The method includes: (a) receiving a hearing test adapter from a plurality of hearing test adapters shipped to a plurality of different patient sites; (b) receiving first device identification data uniquely identifying a first hearing test adapter at a first patient site from among the plurality of different patient sites; (c) transmitting the first device identification data from the first hearing test adapter to a web portal remote from the first patient site; (d) transmitting a first access request from a first user at the first patient site to the web portal requesting a first hearing testing session; (e) responsive to the first access request, receiving a first user interface at the first patient site from the web portal that is customized based on access permissions for the first user, wherein the access permissions permit the first user to provide hearing test feedback responsive to operation of the first hearing test adapter; (f) receiving from the web portal an indication that a first test session has been created; (g) receiving a first control operation associated with the first test session from the web portal; (h) responsive to receiving the first control operation, transmitting a first operational command to the first hearing test adapter, wherein the operational command changes an operation of the first hearing test adapter; and (i) responsive to the change in the operation of the first hearing test adapter, transmitting first test feedback from the first user to the web portal.

In some embodiments, the method includes the following steps at least some of which are carried out concurrently with steps (b) through (i): receiving second device identification data uniquely identifying a second hearing test adapter at a second patient site from among the plurality of different patient sites; transmitting the second device identification data from the second hearing test adapter to a web portal remote from the second patient site; transmitting a second access request from a second user at the second patient site to the web portal requesting a second hearing testing session; responsive to the second access request, receiving a second user interface at the second patient site from the web portal that is customized based on access permissions for the second user, wherein the electronically receiving device identification data access permissions permit the second user to provide hearing test feedback responsive to operation of the second hearing test adapter; receiving from the web portal an indication that a second test session has been created; receiving a second control operation associated with the second test session from the web portal; responsive to receiving the second control operation, transmitting a second operational command to the second hearing test adapter, wherein the second operational command changes an operation of the second hearing test adapter; and responsive to the change in the operation of the second hearing test adapter, transmitting second test feedback from the second user to the web portal.

In some embodiments, receiving the first device identification data uniquely identifying the first hearing test adapter comprises receiving the first device identification data from the first hearing test adapter coupled via an electronic interface between the first hearing test adapter and a first electronic device at the first patient site.

In some embodiments, the method includes: communicating with a microphone coupled to a first electronic device at the first patient site and/or coupled to the first hearing test adapter to receive measurements of environmental noise at the first patient site; selecting an output device of a plurality of output devices to be coupled to the first hearing test adapter responsive to the received measurements of the environmental noise; and/or prior to transmitting the first operational command to the first hearing test adapter, providing an electronic message to the first user indicating the output device to be coupled to the first hearing test adapter. The method may include adjusting the first operational command transmitted to the first hearing test adapter responsive to the received measurements of the environmental noise.

In some embodiments, the first operational command changes the operation of the first hearing test adapter to alter an audio frequency of a tone transmitted into an ear of the first user.

In some embodiments, the method includes inserting an in-ear test probe into an ear of the first user, wherein the first operational command changes the operation of the first hearing test adapter and/or the test probe to alter an internal pressure of the ear of the first user. Altering the internal pressure of the ear of the first user may include increasing a pressure of the internal pressure of the ear of the first user with respect to an atmospheric pressure including operating a manometer and/or a pump associated with the test probe.

In some embodiments, the method includes providing a transducer that is configured to be inserted in or placed on an ear of the first user and a plurality of electrodes that are configured to be placed on the first user's face and/or head. The first operational command may change the operation of the first hearing test adapter and/or the transducer to output a click, tone or speech sound using the transducer. The method may include transmitting from the first patient site to the web portal data gathered from the electrodes that is in response to the click, tone or speech sound.

In some embodiments, the method includes transmitting first multimedia communications to the web portal during the first test session, wherein transmitting multimedia communications comprises transmitting speech of the first user captured by a first electronic device at the first patient site and/or the first hearing test adapter during the first test session.

Some other embodiments of the invention are directed to a medical hearing test system. The system includes: a first computing device at a patient site; a test probe configured to be inserted into an ear canal of a patient at the patient site; and a hearing test adapter configured to be communicatively coupled to the test probe and a first computing device at the patient site. The first computing device is configured to perform operations including: transmitting an access request requesting a hearing testing session from the first computing device to a web portal on a second computing device over an electronic communications network between the first computing device and the second computing device; responsive to the access request, receiving a user interface from the web portal that is customized based on access permissions for the patient, wherein the access permissions permit the patient to provide hearing test feedback responsive to operation of the hearing test adapter; receiving a control operation for the test probe from the web portal over the electronic communications network; responsive to receiving the control operation, transmitting an operational command to the hearing test adapter, wherein the operational command changes an operation of the test probe; receiving a response command from the hearing test adapter responsive to the operational command; and responsive to receiving the response command from the hearing test adapter, transmitting test feedback from the patient to the web portal over the electronic communications network.

In some embodiments, the hearing test adapter is configured to perform operations including: receiving the operational command from the first computing device; translating the operational command to a data communication to the test probe; and/or electronically communicating the data communication to the test probe In some embodiments, the hearing test adapter is included within an audiometer coupled to the first computing device.

In some embodiments, the first computing device is further configured to perform operations including: receiving device identification data uniquely identifying the hearing test adapter; and transmitting the device identification data from the hearing test adapter to a web portal remote from the first computing device, wherein receiving the device identification data uniquely identifying the hearing test adapter comprises receiving the device identification data uniquely from the hearing test adapter over a second electronic communication network different from the first electronic communication network.

In some embodiments, the system includes a microphone coupled to the electronic device and configured to receive measurements of environmental noise. The hearing test adapter may be configured to perform operations including: communicating with the microphone to receive measurements of environmental noise; selecting an output device of a plurality of output devices to be coupled to the hearing test adapter responsive to the received measurements of the environmental noise; prior to transmitting the operational command to the hearing test adapter, providing an electronic message indicating the output device to be coupled to the hearing test adapter; and/or adjusting the operational command transmitted to the hearing test adapter responsive to the received measurements of the environmental noise.

In some embodiments, the operational command changes the operation of the hearing test adapter to alter an audio frequency of a tone transmitted by the test probe into the ear canal of the patient.

In some embodiments, the test probe includes a manometer operatively associated with a pump, and wherein the operational command changes the operation of the hearing test adapter to alter an internal pressure of the ear canal of the patient using the manometer and/or the pump. Altering the internal pressure of the ear of the patient may include increasing the internal pressure of the ear canal of the patient with respect to an atmospheric pressure of the patient.

Embodiments of the present invention provide a web-based service that hosts a system allowing a distributed network of users using client-server architecture. Management and support of the server system can be separate from audiologists and patients. The system can allow users with different access privileges to communicate and interact with the system in different ways.

Embodiments of the invention are directed to methods for performing hearing evaluation tests using test adapters at local patient test sites and a computer network. The methods include: (a) providing a web-based service that provides a diagnostic hearing test system with at least one server that programmatically allows patient and registered audiologist users that are remote from each other to communicate during a hearing test, the web-based service having electronically defined different access privileges for different users, including patient users, administrative users including financial and system maintenance users, and clinical users. Different types of administrative users have different access privileges defined by function, and clinical services performed by clinical users are separate from financial and system maintenance services performed by administrative users. The methods can also include: (b) accepting electronic input from patients to communicate with the web-based service to request a test, schedule a test and/or take a test; and (c) allowing a registered audiologist to communicate with a patient to carry out a hearing test and control an associated local audiometer at a patient site using the web-based service during a test session. Multiple patient and audiologist users can access the web-based service simultaneously to allow multiple concurrent hearing tests to be carried out.

The method may optionally include coordinating the preparation and/or monitoring or facilitating the administration of the hearing test using online multimedia communications. Online media communications can allow an audiologist to interact with the patient orally and/or visually to ensure that the patient is properly prepared before commencing with the hearing test, to synchronize and coordinate the hearing test by responding to feedback from the patient, and/or to generally facilitate the administration of the hearing test (which may allow the hearing test to be conducted in an efficient and timely fashion).

The method may optionally include shipping a test adapter that includes or is in communication with an audiometer to a patient prior to the test session. The audiologist can transmit commands that control operation of the audiometer using the test adapter and web-based service.

In some embodiments, the web-based service is configured to electronically select an audiologist from a list of registered audiologists to perform a hearing test for a patient based on patient geographic location and/or requested test times. The web-based service may be configured to electronically select an audiologist to perform a hearing test only if the audiologist has a current professional license for a state and/or country location where the patient is located.

Other embodiments are directed to telehearing systems that include at least one web server in communication with a global computer network configured to provide a web-based service that hosts a telehearing diagnostic testing system and a plurality of web clients in different physical locations in communication with the at least one server. The plurality of clients includes different users with different access levels, including a plurality of audiologists at different geographical locations. The systems also include a plurality of portable test adapters, each configured to connect a respective patient user to the global computer network at a patient site. The test adapters are configured to: (a) convert data from an audiometer at the patient site and transmit the converted data over the global computer network to a web client associated with a remote audiologist; and (b) convert operational command data from the web client associated with the remote audiologist to control operation of the respective audiometer at the patient site.

The test adapters can be configured to connect (wirelessly or in a wired manner) to a conventional, commercially available audiometer or may include an on-board integrated audiometer.

Embodiments of the present invention employ a test adapter that connects to the Internet (wirelessly or in a "wired" manner). The test adapter communicates with an audiometer that may be a separate component or that may be integral to the test adapter.

The test can be administered by audiologists or clinicians at different sites remote from the respective patients, in a manner which can allow interaction between the patient and the clinician during at least a portion of the administration of the test (e.g., for only a portion of the test or for the whole test). The diagnostic hearing tests can be performed such that they meet standardized guidelines such as ANSI requirements or regulatory or certification standards.

As will be appreciated by those of skill in the art in light of the above discussion, the present invention may be embodied as methods, systems and/or computer program products or combinations of same. In addition, it is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

BRIEF DESCRIPTION OF THE DRAWINGS

FIGS. 13A-13C illustrate exemplary web pages according to embodiments of the present invention.

DETAILED DESCRIPTION OF EMBODIMENTS OF THE INVENTION

Figure 1:
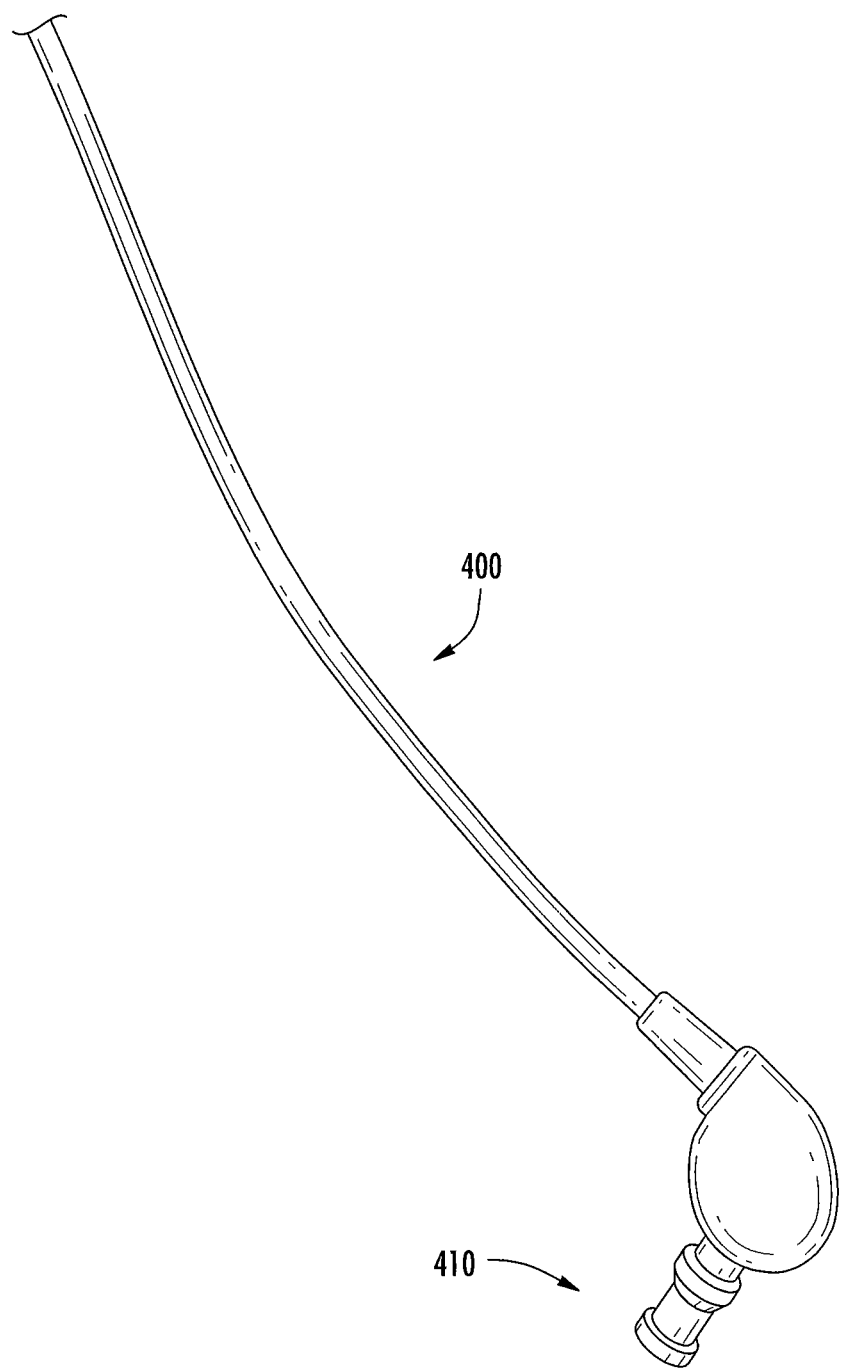
FIG. 1 illustrates a hearing test probe that is configured to be inserted in the ear canal of a patient according to embodiments of the present invention.

The present invention will now be described more fully hereinafter with reference to the accompanying figures, in which preferred embodiments of the invention are shown. This invention may, however, be embodied in many different forms and should not be construed as limited to the embodiments set forth herein.

Like numbers refer to like elements throughout. In the figures, layers, regions, or components may be exaggerated for clarity. Broken lines illustrate optional features or operations unless specified otherwise.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention. The sequence of operations (or steps) is not limited to the order presented in the claims or figures unless specifically indicated otherwise.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

The term "patient" refers to the individual(s) being tested and can include the user or client at the local patient testing site. As used herein, the term "substantially real time" means receiving and/or transmitting data between sites during the test accounting for system delays in remote transmission between sites which may be on the order of seconds or less or potentially minutes in length as a result of routing, traffic, transmission route and/or system communication link employed which can impede the transfer such that slight delays may occur.

The term "automatic" means that substantially all or all of the operations so described can be carried out without the assistance and/or manual input of a human operator. The term "electronic" means that the system, operation or device can communicate using any suitable electronic media and typically employs programmatically controlling the communication between participants using a computer network. The term "programmatically" means the action is directed via a computer program code. The term "hub" means a node and/or control site (or sites) that controls and/or hosts data exchange between different user sites using a computer network. The term "HIPAA" refers to the United States laws defined by the Health Insurance Portability and Accountability Act.

The terms "healthcare data" and "clinical data" and "patient records" are used interchangeably and include any and/or all of a treatment, medicinal, drug or prescription use, laboratory tests and/or results, diagnostic information, demographic information, a physical location, a home address (such as a zip code), insurance information other relevant data associated with a patient.

The term "registered" means that the user is a recognized participant of the system. The term "administrative user" refers to a user that does not perform clinical actions or clinical services and is typically a user that does not have permission to access patient medical records. Different types of administrative users can have different access levels to the system. The term "web-based" means that the service uses at least one server to communicate with different users over the World Wide Web, typically via the hypertext transfer protocol (HTTP).

Embodiments of the invention may use a computing architecture in which the user interface, the application processing logic, and/or the underlying database(s) can be encapsulated in logically-separate processes. In any given application utilizing this type of computing architecture, the number of tiers may vary depending on the requirements of the particular application; thus, such applications are generally described as employing an n-tier architecture. See, e.g., Exforsys.com, N-Tier Client-Server Architecture. For instance, some embodiments of the invention may employ a 2-tier architecture, commonly referred to as a client-server architecture, wherein a client application such as a web browser makes a request from a web server, which processes the request and returns the desired response (in this case, web pages). Other embodiments of the invention may be structured as a 3-tier or other larger multi-tier architecture, wherein the web server provides the user interface by generating web pages requested by a web browser, which receives and displays code in a recognized language such as dynamic HTML (Hypertext Markup Language); middleware executing on an application server handles the business logic; and database servers manage data functions. Often, the business logic tier may be refined into further separate tiers to enhance manageability, scalability, and/or security.

Accordingly, in some web-based hearings services, the web applications can use a 3-tier architecture with a presentation tier, a business logic tier, and a patient record data tier. The web application tiers may be implemented on a single application server, or may be distributed over a plurality of application servers. The presentation tier can provide web pages that allow a user to request hearing test services, schedule the test services, and allow communication between the patient user and the remote audiologist user during the hearing test session. The presentation tier may communicate with other tiers in the application such as the business logic tier and/or patient record data tier by accessing available components or web services provided by one or more of the other application tiers. The presentation tier may communicate with another tier to allow authorized users to access patient record data and/or database stored procedures, instructions, or protocols. The business logic tier can coordinate the application's functionality by processing commands, scheduling tests and evaluating data. The functionality of the business logic tier may be made accessible to other application tiers by, for example, the use of web services. The business logic tier may also provide the logic, instructions or security that can separate and distinguish clinical users from non-clinical users (e.g., administrative users). The patient data record tier can hold the private patient records data and encapsulate such records from unapproved parties so as to comply with the Health Insurance Portability and Accountability Act (HIPAA) or other privacy regulations. The patient records data tier can make data available through, for example, stored procedures, logic, instructions and the like accessible, for example, by web services.

As will be appreciated by one of skill in the art, embodiments of the invention may be embodied as a method, system, data processing system, or computer program product. Accordingly, the present invention may take the form of an entirely software embodiment or an embodiment combining software and hardware aspects, all generally referred to herein as a "circuit" or "module." Furthermore, the present invention may take the form of a computer program product on a computer-usable storage medium having computer-usable program code embodied in the medium. Any suitable computer readable medium may be utilized including hard disks, CD-ROMs, optical storage devices, a transmission media such as those supporting the Internet or an intranet, or magnetic or other electronic storage devices.

Computer program code for carrying out operations of the present invention may be written in an object oriented programming language such as Java, Smalltalk, C# or C++. However, the computer program code for carrying out operations of the present invention may also be written in conventional procedural programming languages, such as the "C" programming language or in a visually oriented programming environment, such as Visual Basic.

Certain of the program code may execute entirely on one or more of a user's computer, partly on the user's computer, as a stand-alone software package, partly on the user's computer and partly on a remote computer or entirely on the remote computer. In the latter scenario, the remote computer may be connected to the user's computer through a local area network (LAN) or a wide area network (WAN), or the connection may be made to an external computer (for example, through the Internet using an Internet Service Provider). Typically, some program code executes on at least one web (hub) server and some may execute on at least one web client and with communication between the server(s) and clients using the Internet.

The invention is described in part below with reference to flowchart illustrations and/or block diagrams of methods, systems, computer program products and data and/or system architecture structures according to embodiments of the invention. It will be understood that each block of the illustrations, and/or combinations of blocks, can be implemented by computer program instructions. These computer program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the block or blocks.

These computer program instructions may also be stored in a computer-readable memory or storage that can direct a computer or other programmable data processing apparatus to function in a particular manner, such that the instructions stored in the computer-readable memory or storage produce an article of manufacture including instruction means which implement the function/act specified in the block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the block or blocks.

As noted above, the present invention provides systems, methods and associated devices for performing diagnostic hearing tests which use a computer network with a distributed, client-server architecture to allow interaction between remote sites and ("local") patient sites.

Figure 6A:
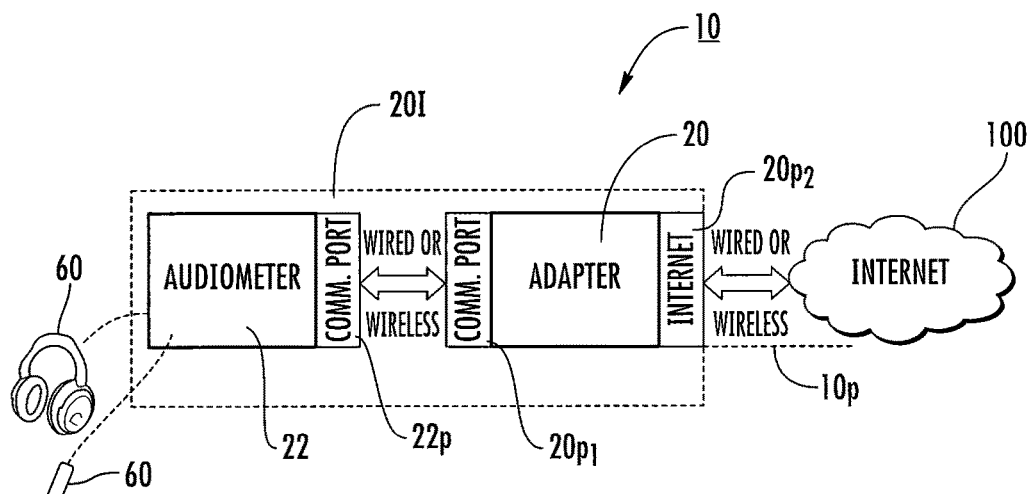
FIG. 6A is a block diagram of a test/communication adapter that communicates using the Internet according to embodiments of the present invention.
Figure 7:
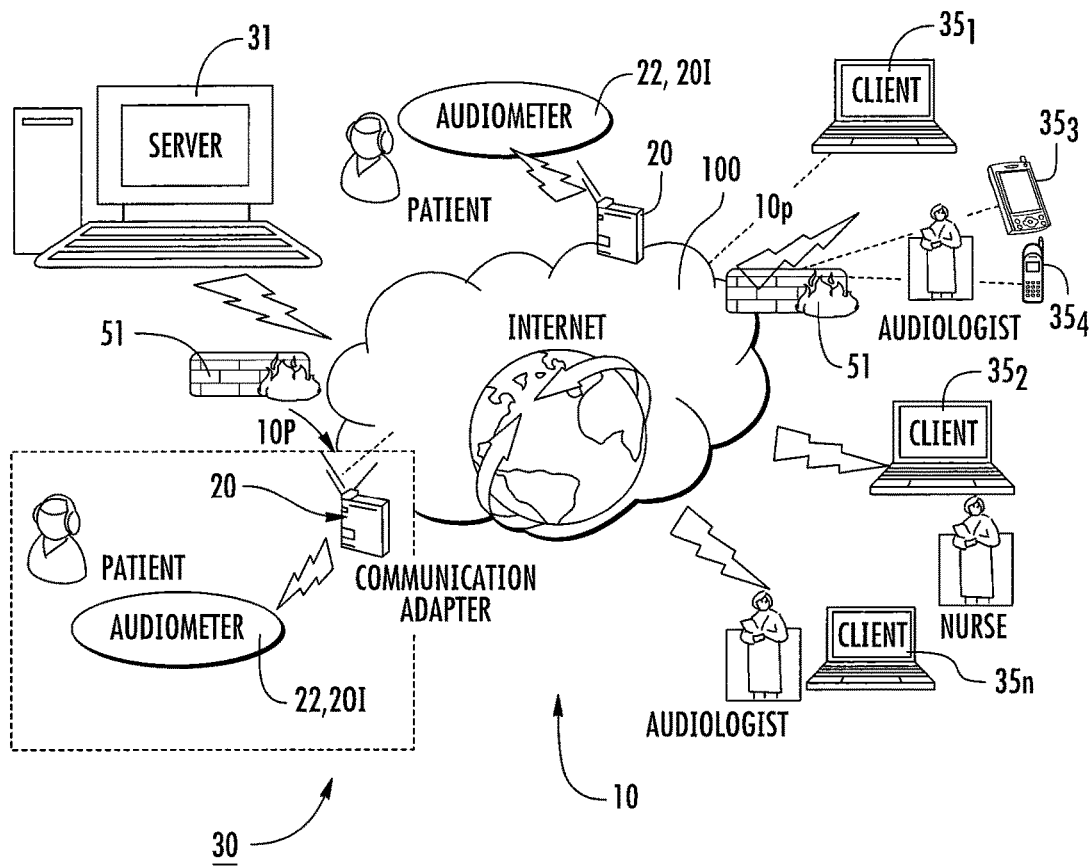
FIG. 7 is a block diagram of a telehearing system having client-server architecture according to embodiments of the present invention.

Referring to FIG. 6A, embodiments of the present invention provide systems 10 that allow for remote hearing diagnosis. The systems 10 can include a portable test adapter 20 that connects an audiometer 22 to the Internet 100. The test adapter 20 can include an "on-board" or integral audiometer 20I or the test adapter 20 can connect to an off-the-shelf or standard audiometer 22 (the latter of which does not have Internet access capability), either way so as to connect the audiometer to a global computer network, e.g., the Internet. The systems 10 also include a web-based diagnosis system having a client-server architecture 30 (FIG. 7). The audiometer 22 can be in communication with a hearing output device 60 such as earphones or an ear probe assembly that may be configured to be a single use disposable device, being initially sterilized for sterile testing conditions. For example, a single use, disposable (cost effective) ITE-or earplug design can be used either for a biotelemetry reading and/or for the tone output.

Conventional audiometers 22 have certain data exchange capability (either hardwired or wirelessly). See, e.g., U.S. Pat. No. 7,370,533, the contents of which are hereby incorporated by reference as if recited in full herein, and the OTOPod audiometer from Otovation, LLC, of King of Prussia, P.A., which uses the Bluetooth wireless protocol to exchange data with a computer. Through this connection, audiologists can operate the audiometer and receive hearing data from the audiometer 22. To allow remote diagnosis function over the Internet 100, the test adapter 20 can convert data from an audiometer 22 to TCP/IP packets (which are in turn sent to the audiologist over the Internet 100) and also convert operational commands from an audiologist (in TCP/IP packets) into a format that can be accepted by the audiometer. Alternatively, the test adapter 20I can be configured to perform these functions for the on-board audiometer 22. Depending on the communication port $22p$ on the conventional audiometer 22 or the configuration of the on-board audiometer 22 in the integrated test adapter 20I, the connection $20p_1$ between the adapter 20 or 20I and the audiometer 22 can be hardwired (e.g., RS-232 or USB) and/or wireless (e.g., using a wireless protocol such as Bluetooth or Zigbee) or configured to operate both ways to allow a user to select either. The test adapter connection $20p_2$ to the Internet 100 can also be wired or wireless and may be configured to be operate both ways to allow for a user to select either to facilitate different patient preferences. The Internet 100 can be accessed via any desired device having access to the Internet including wireless communication systems (such as cellular telephones), PDAs, desktop or portable computers including lap or handheld computers and the like.

In some embodiments, a particular patient test site can use a dedicated test adapter 20 and/or audiometer. In some embodiments, the system 10 can be configured to provide a test adapter 20 to a patient user for use at any desired location having access to the Internet 100. In some embodiments, the system 10 is configured to ship the test adapter 20 and audiometer 22, or the integrated version 20I, to a patient's residence. After the test, the adapter 20, 20I can be returned, such as using a pre-paid mailing package (properly insulated for weather and protection), courier or shipment pick-up, or physical drop-off at a shipping center or at a return center. In other embodiments, a local facility, such as a hospital, doctor's practice or other "community" location, may have an inventory of the devices 20 (and 22) and/or 20I that can be loaned to registered patients for use.

Calibration and proper operation of the audiometers 22 and/or test adapters 20, 20I, can be performed after each use and prepared for subsequent use. The use, status, and location of the devices 20, 22, 20I can be tracked for inventory control. For example, if a patient has a scheduled hearing test, the adapter 20, 20I can be shipped to that patient in advance of the test and identified as "at patient site" with an associated scheduled test date and expected return date to allow for inventory management. Courtesy reminders can be sent electronically and/or telephonically regarding a scheduled test time. Reminders can also be sent right after the test date and again if a device (20, 22, 20I) has not been returned within a defined period. Charges for "overdue" units can be applied to patients that are not prompt. A patient may be required to sign a contract to that effect; such a contract can be provided as a condition to use the system 10 (such as a point and click or electronic signature upon registering as a participating patient).

Figure 6B:
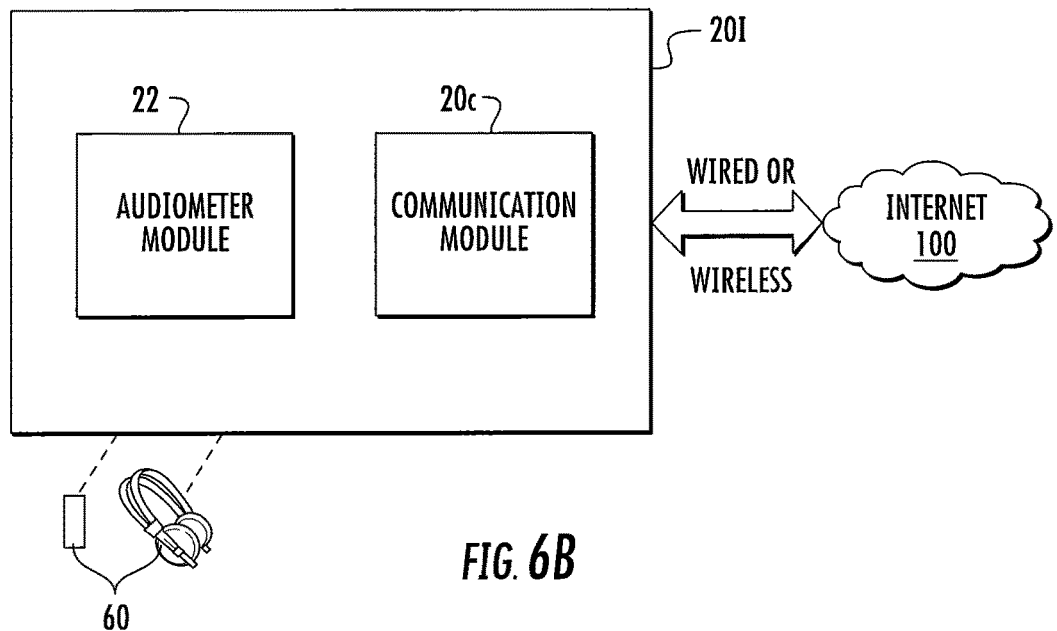
FIG. 6B is a block diagram of an integrated test adapter that communicates using the Internet according to embodiments of the present invention.

Referring to FIG. 6B, the integrated test adapter 20I may integrate the audiometer 22 as part of an electronic device. In some embodiments, the electronic device is a portable electronic device such as a smartphone or a tablet computer. The audiometer 22 may execute, in part, as a software module within the integrated test adapter 20I. The integrated test adapter 20I may further include a communication module 20c capable of connecting to the Internet 100. The communication module 20c may also execute, in part, as a software module within the integrated adapter 20I. The communication module 20c may, in some embodiments, perform the conversion of operational commands from an audiologist (in TCP/IP packets) into a format that can be accepted by the audiometer 22. In other words, the communication module 20c may perform, using software operations many or all of the operations of the test adapter 20 as described with respect to FIG. 6A. The integrated test adapter 20I may include connections capable of interfacing with input/output devices 60. The integrated test adapter 20I may include identification data that uniquely identifies the adapter (e.g., serial number, part number, revision number, manufacturer and the like). The integrated test adapter 20I may be able to control the software module performing the function of an audiometer 22. In some embodiments, the integrated test adapter 20I may be able to control additional peripherals for performing hearing tests as described herein. In addition to controlling the peripherals, the integrated test adapter may be able to communicate results and/or data collected from the peripherals (e.g., input/output devices 60) to the Internet 100 via the communication module 20c. Similarly, operational commands and/or data received from the Internet 100 may be received by the communication module 20c and communicated to the peripherals (e.g., input/output devices 60).

Referring to FIG. 7, the system 10 includes at least one web server 31 and a plurality of web clients $35_1$-35n (with "n" being an integer number corresponding to the number of participating or registered users). Typically, "n" is greater than 10; more typically, n is between 100-10,000, or even more, corresponding to the number of registered users (not including patient users). Some of the users, e.g., at least the audiologist user 40, can communicate with the system 10 via any suitable device having website browsing capability, including, for example, PDAs $35_3$ and cellular telephones $35_4$ as shown in FIG. 7. Thus, the audiologist user 40 can communicate with the patient user 50 during a hearing test via the Internet 100 using a PDA (personal digital assistant) or cellular telephone (shown with $35_3$, $35_4$) having web-browsing capability (or palm, laptop or desktop computer 370 (FIG. 10B)).

The at least one web server 31 can include a single web server as a control node (hub) or may include a plurality of servers (not shown). The system 10 can also include routers (not shown). For example, a router can coordinate privacy rules on data exchange or access. Where more than one server is used, different servers (and/or routers) may execute different tasks or may share tasks or portions of tasks. For example, the system 10 can include one or combinations of more than one of the following: a security management server, a registered participant/user directory server, a patient record management server, a scheduling server, an inventory tracking server, and the like. The system 10 can include firewalls 51 and other secure connection and communication protocols. For Internet based applications, the server 31 and/or at least some of the associated web clients 35 can be configured to operate using SSL (Secure Sockets Layer) and a high level of encryption. Furthermore, given the ubiquitous nature of the Internet, test devices may readily be moved from site to site. Additionally, additional security functionality may also be provided. For example, incorporation of a communication protocol stack at the client and the server supporting SSL communications or Virtual Private Network (VPN) technology such as Internet Protocol Security Architecture (IPSec) may provide for secure communications between the patient sites and the test administration sites to thereby assure a patient's privacy.

As shown in FIGS. 6A, 6B, and 7, the systems 10 may include a web portal 10p that controls participant access. The web portal 10p may also communicate with the server 31 that controls traffic. The web portal 10p may be configured to be user-specific based on defined privacy or privilege levels of the user. That is, each web client 35 can display a different web portal 10p configuration and/or different web pages associated with a specific user type (showing different permissible actions, commands and data options).

The server 31 can provide a centralized administration and management application. The server 31 can be configured to provide session management, tracing and logging systems management, workload management and member services. The server 31 can include or communicate with a plurality of databases including participant/user profiles, a security directory, routing security rules, and patient records. The server 31 can include several subservers for integration into web systems, such as, but not limited to, a web application server (WAS) which may comprise an IBM WebSphere Application Server, a Directory Server such as a Lightweight Directory Access Protocol (LDAP) directory server, and may include an Anonymous Global Patient Identifier (AGPI) Server, a DB2 Server, and a Simple Mail Transfer Protocol (SMTP) Server. It is noted that although described herein as "servers" other suitable computer configurations may be used. The server 31 can be configured with web application functions that appear at portal sites 10p. The server 31 may comprise and/or be configured as a Web Sphere Business Integration (WBI) server. The web server 31 can include a web-based administration application. The web application can be used to: allow a user to register as a participant, manage Access Control Lists (ACLs), logon using universal ID or password access, logoff, define profile preferences, search, approve test requests, receive test request(s), schedule tests, schedule shipments of test adapters 20 (optionally with 22) or 20I, and the like.

The web clients 35 can be associated with different users and different user categories or types. Each category or type may have a different "privilege" or access level to actions or data associated with the systems 10. For example, the systems 10 can include clinician users, administrative users, and accounting users, each of which can have different access levels or restrictions to data and/or actions allowed by the system.

The web clients 35 can be distributed at different geographic locations in different time zones and states or even countries. In other embodiments, the web clients 35 can be at a single medical center with audiologists that can administer the test. Different user types may be at different geographic locations. For example, one or more of accounting, insurance submission and oversight, inventory management (of the test devices), and scheduling may be handled at different locations from the audiologists. Indeed, a nurse (where used) may be located in a different location from the audiologist and yet work "together" as a clinician team on a particular patient case. The nurse user (where used) may have a different portal configuration than an audiologist user. Similarly, a physician user (where used) may have the same or a different configuration than a nurse and/or audiologist user. In other configurations, the nurse and audiologist use the same web client 35 at the same location, but each includes different log-on identifiers, which gives them different privileges, actions and/or commands associated with the hearing system.

The patient test site can be at a multi-user site, such as a factory or industrial office, a medical related facility, such as a hospital, general practice clinic, or pediatrician's office, nursing home or may be a private residence or other location where a patient has access to the Internet.

Figure 8:
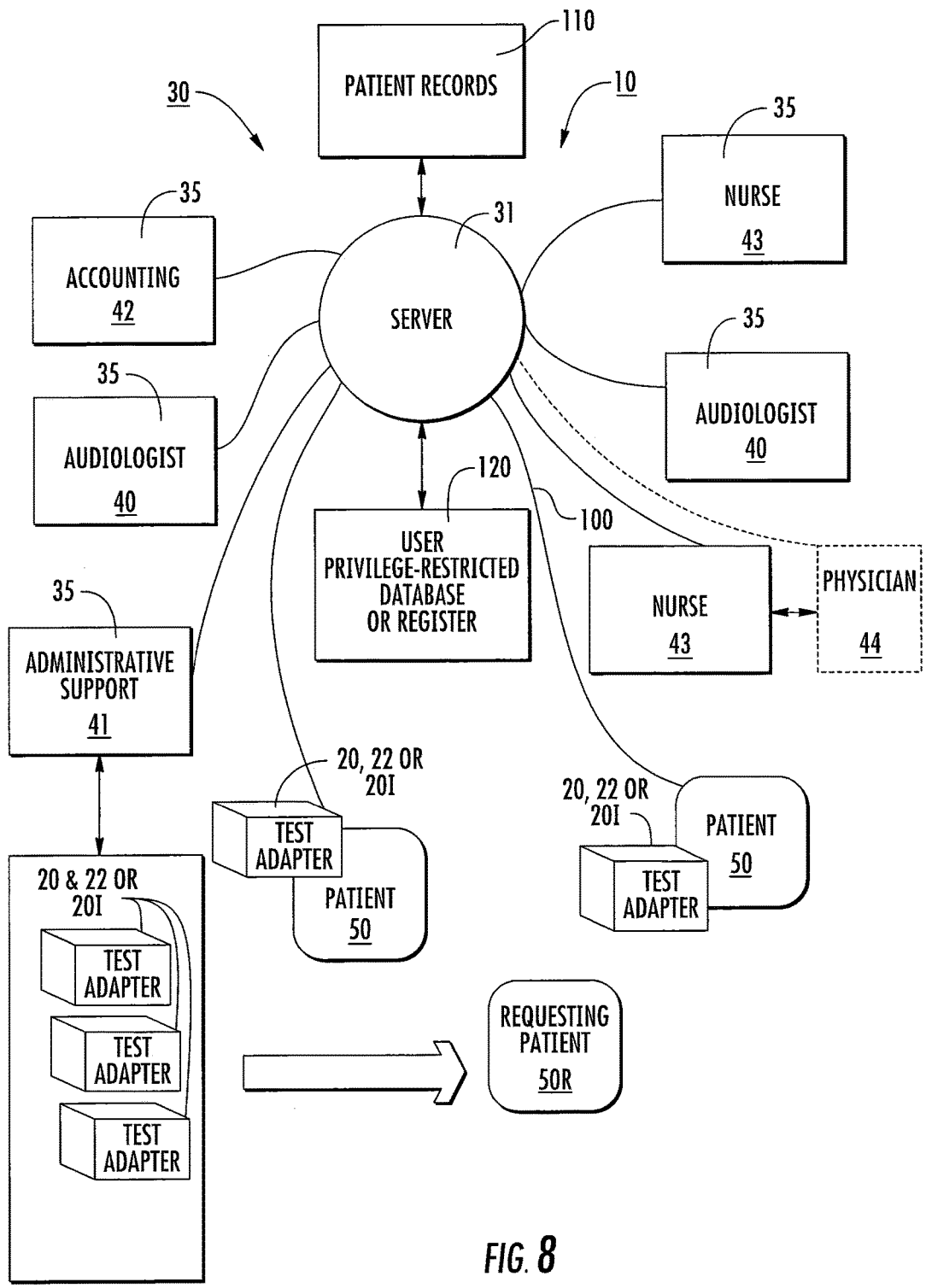
FIG. 8 is a block diagram of a web-based service hosting a telehearing diagnostic system with defined access levels for different users and/or different user categories according to embodiments of the present invention.

Referring to FIGS. 7 and 8, the web-based service system 10 can have a distributed, client-server architecture 30. The term "web-based service" is intended to be interpreted broadly so as to encompass many discrete or different web-based services under the umbrella of the web-based hearing test system 10, typically separating the clinical services from the administrative services, such as from users associated with the management, maintenance, support and financial services. That is, for example, the services related to the management and support of the system 10 can be separated from the services rendered by audiologists to the patients. In some embodiments, under this architecture, patients, audiologists, nurses, and other users (e g., financial workers such as those workers/users in billing, collections or accounting) can log onto the system 10 with different privileges (and possibly with different portal configurations, web pages and/or user interfaces). The different user categories, e.g., audiologists 40, administrative support 41, accounting 42, nurses 43, and optionally, physicians 44, can each have different tasks and different access levels to the system. A nurse 43 and audiologist 40 (and or physician 44) may have the same level of privilege or the audiologist (and physicians 44, where allowed) and nurses 43 may have different levels of access or privileges. They may use the same portal or client or different portals/clients.

In some embodiments, the physician users 44 may be configured to communicate with the system 10 independent of an assistant, such a nurse (e.g., in parallel) or may be configured to access the system 10 after an assistant, (e.g., in series) or other user requests medical evaluation by the physician. To facilitate timely intervention, the physician session can be scheduled while the patient-user is being tested by the audiologist or shortly after a hearing test when a patient user can still be on-line and accessible, e.g., proximate in time to a hearing test session (such as within 10-60 minutes after such a test session), typically upon referral via a nurse or audiologist. The system 10 may allow physicians to identify their available status using a web page. The system 10 can identify a queue of available physicians and update that queue so that physicians can connect into the system in a timely manner. The physician session can be remotely carried out in substantially real time after the audiologist or nurse requests a medical evaluation if a nurse or audiologist user determines that such is a desired action based on information obtained during a hearing test. The physician 44 can access the system 10 to review a patient's records and/or interview and communicate with the patient user for further evaluation. In some embodiments, the physician 44 and audiologist 40 or nurse 43 can be in communication with each other participate in the medical evaluation. Alternatively, the medical evaluation can be summarized and sent to the audiologist forming a medical record after the audiologist has terminated a hearing test session.

The distributed structure can promote increased efficiency in management by tracking transactions through the at least one server 31. The system 10 can support multiple hearing tests at different user sites including clinical users, audiologists 40, nurses 43, physicians 44 (or physician assistants), where used, patients 50 and administrative users 41 concurrently.

As shown in FIG. 8, the system 10 can include a patient record database and/or server 110 as well as a user privilege based and/or restricted access registry 120. The patient record database and/or server 110 can include electronic medical records (EMR) with privacy access restrictions that are in compliance with HIPAA rules due to the client-server operation and privilege defined access for different users. The hearing tests can be performed using the system 10 while allowing interactions between users 50, 40 in a substantially real-time manner.

FIG. 8 also illustrates that the test adapter 20 (and optionally a separate audiometer 22) or integrated test adapter 20I can be matched to a requesting patient 50R in advance of a scheduled test date. The administrative support user 41 can be directed to ship or provide the test adapter 20, 20I to the patient based on the scheduled test date or request for a test by a participating (and approved or registered) patient 50. The inventory management system can be managed by the administrative support function 41, which can include an electronically tracked queue of inventory as well as status and projected and actual use. The support function 41 can also send the test reminders, return reminders, and track shipments, returns and pick-ups.

Figure 9:
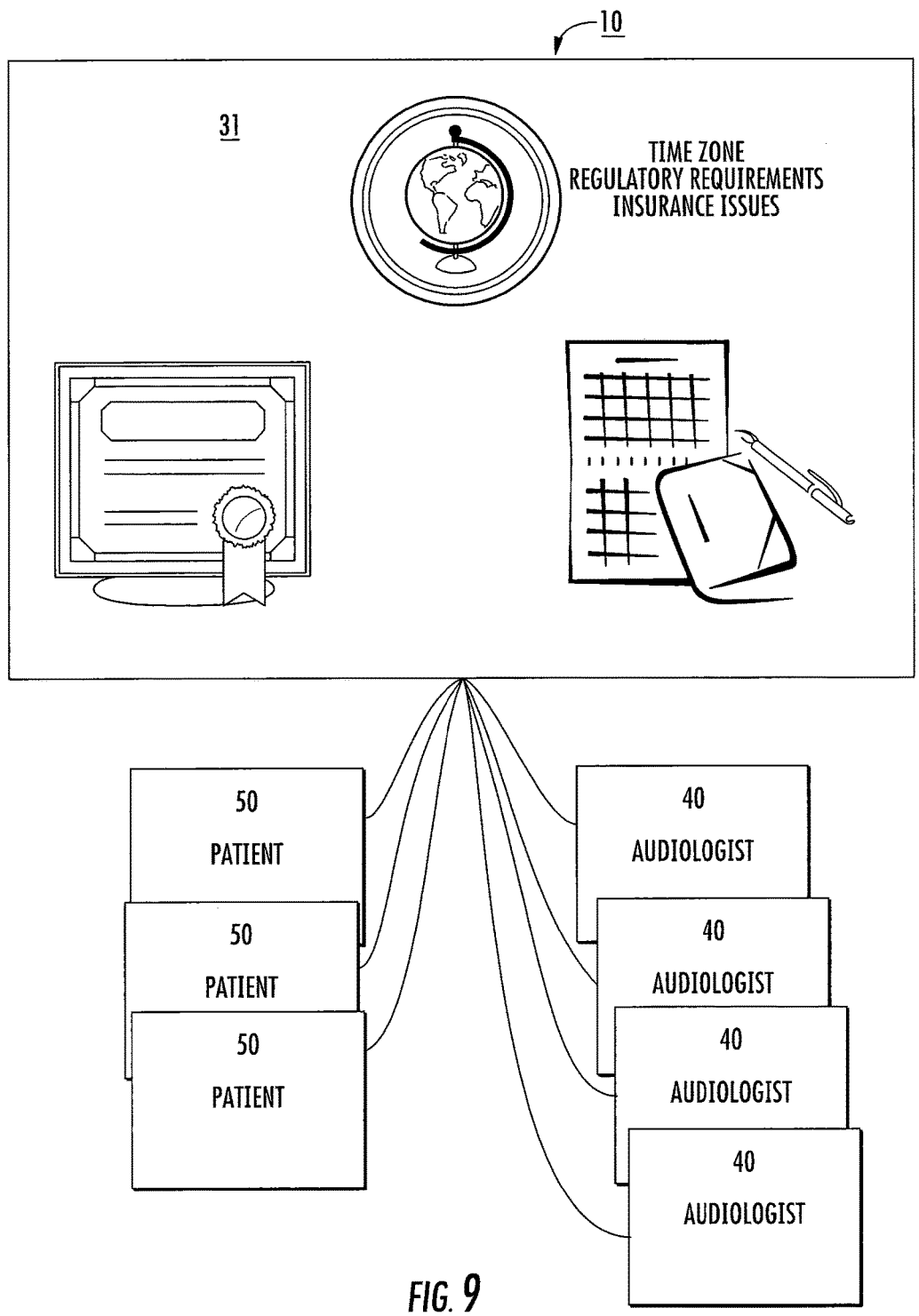
FIG. 9 is a schematic illustration of exemplary operations of the web-based service according to embodiments of the present invention.

FIG. 9 illustrates that the server 31 can pair patient users 50 with audiologist users 40 for hearing tests. The server 31 (or subservers, databases or other servers in communication therewith) can match a patient's geographic location, time zone, insurance compatibility issues and schedule preferences (if provided) to a registered audiologist that is in that same geographic location and/or time zone or a compatible time zone and has openings (dates and times) that meet scheduling parameters. In some embodiments, the system 10 can be configured to define what states, countries or appropriate jurisdictions that a registered audiologist is licensed to practice in (where such states have those requirements for practicing medicine on its citizens or on patients within its borders) and is in good-standing, before selecting the audiologist for scheduling. The system 10 can have a compliance monitoring circuit that can require certificates of compliance and proof of licensure annually or at other intervals. Thus, the system 10 can be able to electronically consider only those registered audiologists licensed in a state associated with the patient, then select one for testing based on those audiologists licensed for that state. After this initial pre-selection, other rankings can be used to select a match (such as audiologist availability, those within the same state, region or zip code) or the system can select via an arbitrary, random or in serial order, an audiologist that is matched to a patient. The system can be configured to allow a patient to be retested using the same audiologist. The system 10 can also provide more than one audiologist "referral" and allow the user/patient to select the one for his/her test.

The test may be requested but not scheduled until a patient has an actual test adapter 20, 20I, at which time the patient may electronically communicate the device indentifying data (e.g., serial number, part number, revision number, manufacturer and the like). The test can then be (promptly) scheduled. In other embodiments, the test is scheduled first, and the test device 20, 22 and/or 20I is then shipped or scheduled for pick-up locally by the patient proximate in time to a scheduled test date.

It is contemplated that different test adapters or audiometers may be used or may be revised over time. The system 10 can be configured to allow for use with different audiometers 22 and different test adapters 20 by providing for a test input that defines what equipment is at the patient site. The system 10 can thus support multiple known equipment configurations while providing the same diagnostic output and modify the control and communication of the test administration based on the knowledge of the tools and the different operational protocols.

Figure 10A:
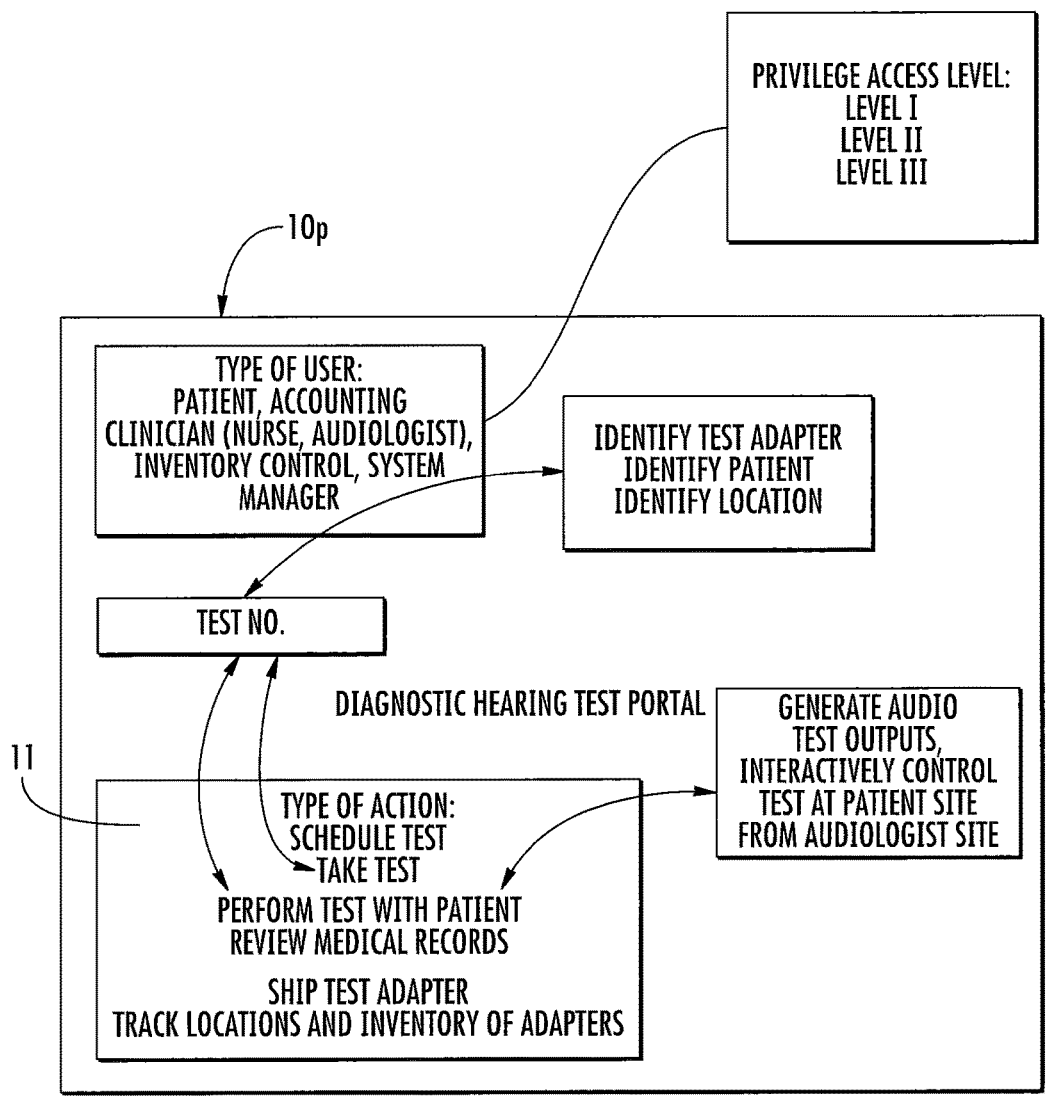
FIG. 10A is a block diagram of an exemplary display of a portal and/or web page with examples of permissible actions according to user-based privilege/access levels according to embodiments of the present invention.

FIG. 10A illustrates an example of a user interface or web portal, which identifies a user type and is correlated to an access level (shown as Levels I-III). For audiologists, the portal can display patient information and location with the type of adapter or other adapter information. Different actions can be selected depending on the user. The portion of the display 11 showing "Type of Action" illustrates three different action types for three different user types. The top is for a patient user, the middle is for an audiologist user, and the lower is for an administrative user. If an audiologist selects the action "perform test", a pop-up menu or subsequent screen can be displayed which allows the audio test output selections.

Figure 10B:
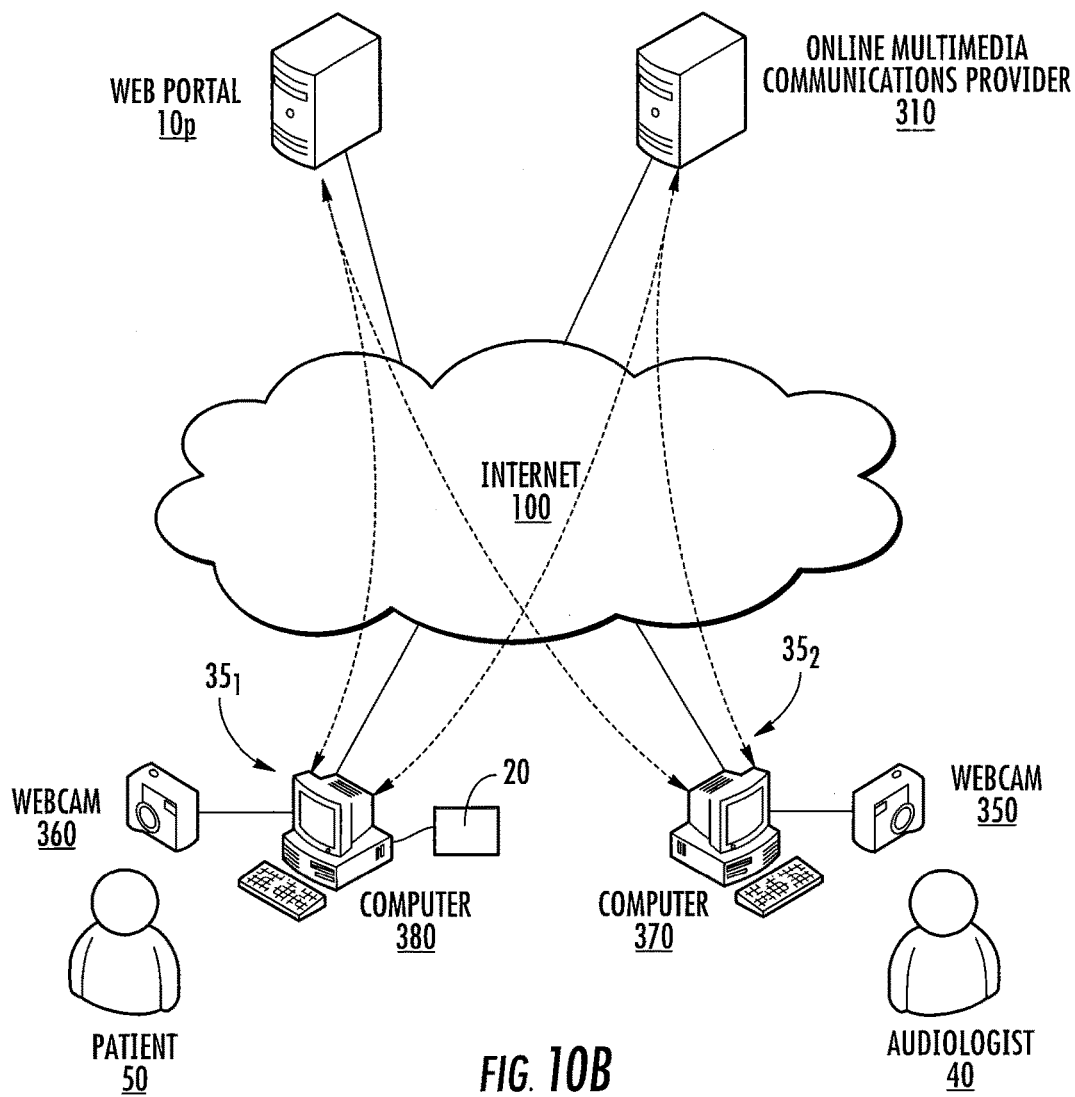
FIG. 10B is a block diagram of a web-based service hosting a telehearing diagnostic system in conjunction with a multimedia communications provider according to embodiments of the present invention.

As illustrated in FIG. 10B, some embodiments of the present invention may allow a patient and an audiologist to access a web portal providing a diagnostic hearing test while using online multimedia communications to synchronize and coordinate the hearing test. Services related to online multimedia communications may be provided by an appropriately secured for health care third-party online multimedia communications service provider 310, which may be, e.g., a consumer videoconferencing service provider such as WebEx, VSee and Evisit, or Vidyo. Audiologist 40 and patient 50 can both access the diagnostic hearing test provided by web portal 10p over the Internet 100. At the same time, webcams 350 and 360, communicatively coupled to computers 370 and 380 used by audiologist 40 and patient 50, respectively, may transmit multimedia communications between audiologist 40 and patient 50 over the Internet 100 via online multimedia communications service provider 310. Once connected to a patient 50 via online multimedia communications service provider 310, an audiologist 40 may use online multimedia communications to facilitate the administration of the hearing test provided by web portal 10p by, e.g., responding to patient inquiries, demonstrating proper use of test equipment, or indicating when patient 50 is to perform test-related activities, allowing visual monitoring of the patient during the hearing assessment and the like. In other embodiments, functionality for providing online multimedia communications may be integrated into the system 10 web portal 10p, such that a separate third-party service provider is unnecessary.

Figure 11:
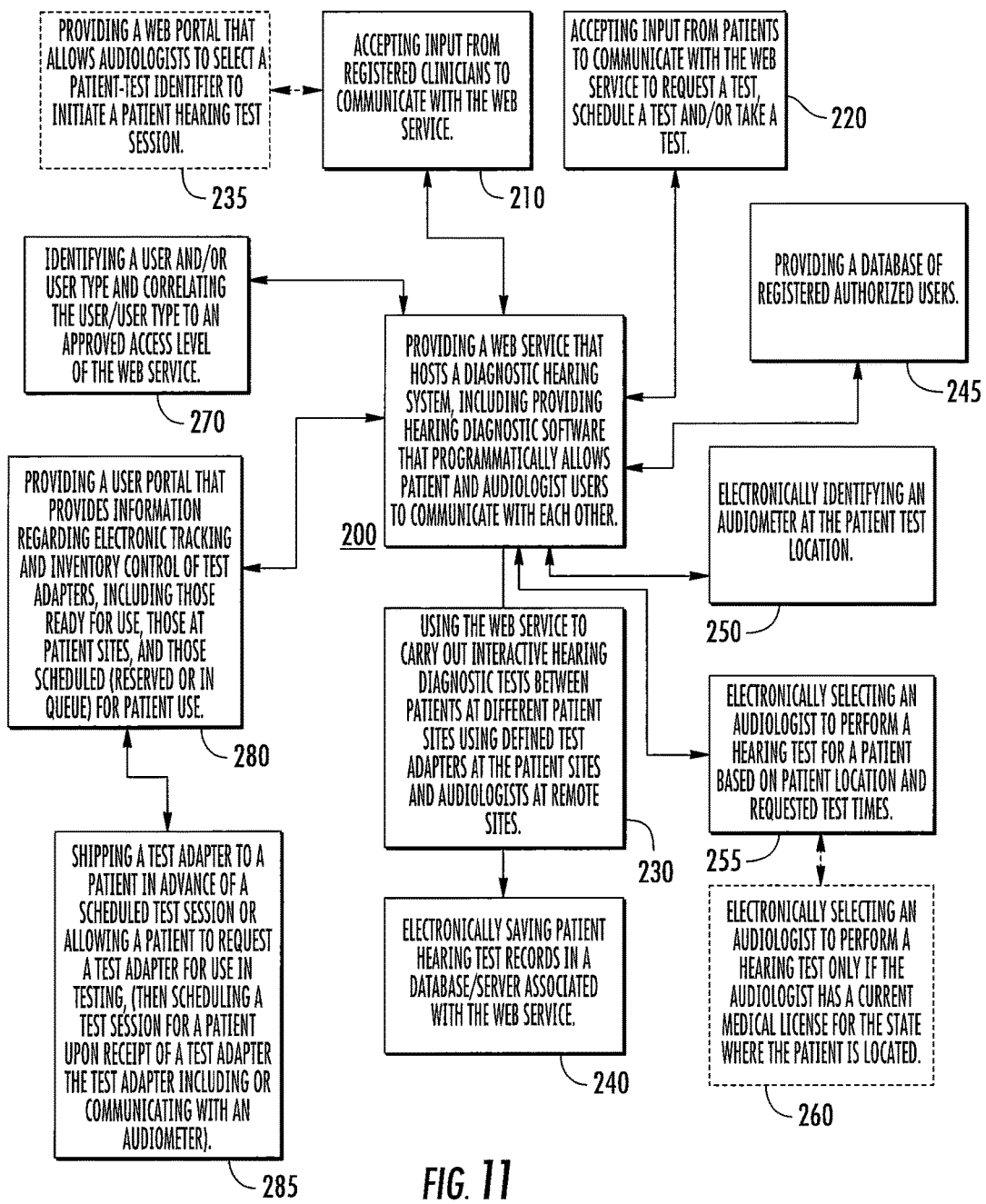
FIG. 11 is a flowchart of operations for performing a hearing diagnostic test according to embodiments of the present invention.

Referring to FIG. 11, in some embodiments, a web-based service can host a diagnostic hearing system (block 200) with at least one server that includes hearing diagnostic software that programmatically allows patients and audiologists to communicate. The service can accept input from registered clinicians to communicate with the web-based service (block 210). The service can accept user input from patients to communicate with the web-based service to request a test, schedule a test, or take a test (block 220). The web-based service allows an interactive hearing test between the clinician and a respective patient (block 230). The service can optionally provide a web portal that allows audiologists to select a patient-test identifier to initiate a hearing test session (block 235).

Patient data records can be electronically saved in a database and/or server associated with the web-based service (block 240). The system can include a database of registered authorized users (block 245) and can be configured to electronically identify an audiometer at the patient test location (block 250). The system can select an audiologist to perform a hearing test for a patient based on patient location and/or test times (block 255). Optionally, the system can select the audiologist only if the audiologist has a current medical license for the state where the patient is located (block 260).

The system can identify a user and/or user category or type and correlate the user/user type to an approved access level (block 270). A user portal provides information regarding electronic tracking and inventory control of test adapters, including those ready for use, those in use and those scheduled for use (in the queue for refurbishment, being returned and/or in preparation (recalibration, etc. . . . ) after a prior test, or reserved for patient use) (block 280). A test adapter can be shipped to a patient test site or a patient in advance of a test session (block 285), e.g., after a test is scheduled or shipping to a patient/patient test site, then upon receipt having the patient electronically confirm that by entering the web portal and entering the device identifier or other identifying information, then having a test date scheduled.

The hearing test can be administered by the registered audiologist user at a test administration site, remote from the patient site in a manner which can allow interaction (typically one or more of a non-verbal, verbal, and/or visual communication interaction either one or two way) between the user and the clinician during at least a portion of the administration of the test. A video input associated with the patient and/or audiologist may also be used to allow one or two-way visual communication. The diagnostic hearing tests can be performed such that they meet or comply with standardized guidelines such as the American National Standards Institute ("ANSI") requirements or other agency or regulatory standards, as desired for the particular testing authority in a particular jurisdiction.

The system 10 can be configured to allow the audiologist to control the test sequence and auditory hearing assessment tones from the remote administration site. Thus, the hearing test can be performed such that the hearing tones (frequency and decibel level) are generated and output locally at the patient site from the test adapter 20I or audiometer 22 in response to commands transmitted from the remote site over the Internet as received by the test adapter 20, 20I that selects the desired tone/level which are transmitted from the expert or test administration site to the local site via the computer network. In turn, the local audiometer 22, based on the received or relayed commands, generates the tones and controls the levels output to the user/patient so that they are output to the patient in a controlled calibrated manner. In certain embodiments, the system is also configured to accept the patient's input or response during the test and transmit the associated data back to the administration site where it can be considered and evaluated. The system can also allow the test administrator (typically an audiologist) to adjust the test sequence or tone based on the patient's indicated response during the testing protocol. Thus, the audiologist can adjust the testing parameters or protocol based on the patient's response during the testing procedure. In so doing, the test administrator can, inter alia: (a) select or adjust the tone transmitted to the patient, (b) repeat one or more of the tones or frequencies, and/or (c) render a diagnostic evaluation.

The system 10 can also be configured to carry out a remote-controlled (internet based) tympanometry examination and/or an otoacoustic emission (OAE) test. Tympanometry tests the condition of the middle ear and/or the mobility of the eardrum (tympanic membrane) and the conduction bones by creating variations of air pressure in the ear canal. Tympanometry is an objective test of middle-ear function. The tympanometry evaluation can be done in conjunction with the hearing (pure tone audiometry) test as it is a measure of energy transmission through the middle ear. In evaluating hearing loss, tympanometry permits a distinction between sensorinueural and conductive hearing loss, when evaluation is not apparent by other testing. Furthermore, tympanometry can be helpful in making the diagnosis of otitis media by demonstrating the presence of a middle ear effusion. OAE measures an acoustic response that is produced by the inner ear (cochlea) which, generally stated, bounces back out of the ear in response to a sound stimulus. The test is typically performed by placing a small probe that contains a microphone and speaker into an infant's ear. A clinician can determine which sounds yielded a response/emission and the strength of those responses. If there is an emission present for those sounds that are critical to speech comprehension, then the infant has "passed" the OAE hearing screen.

Figure 12A:
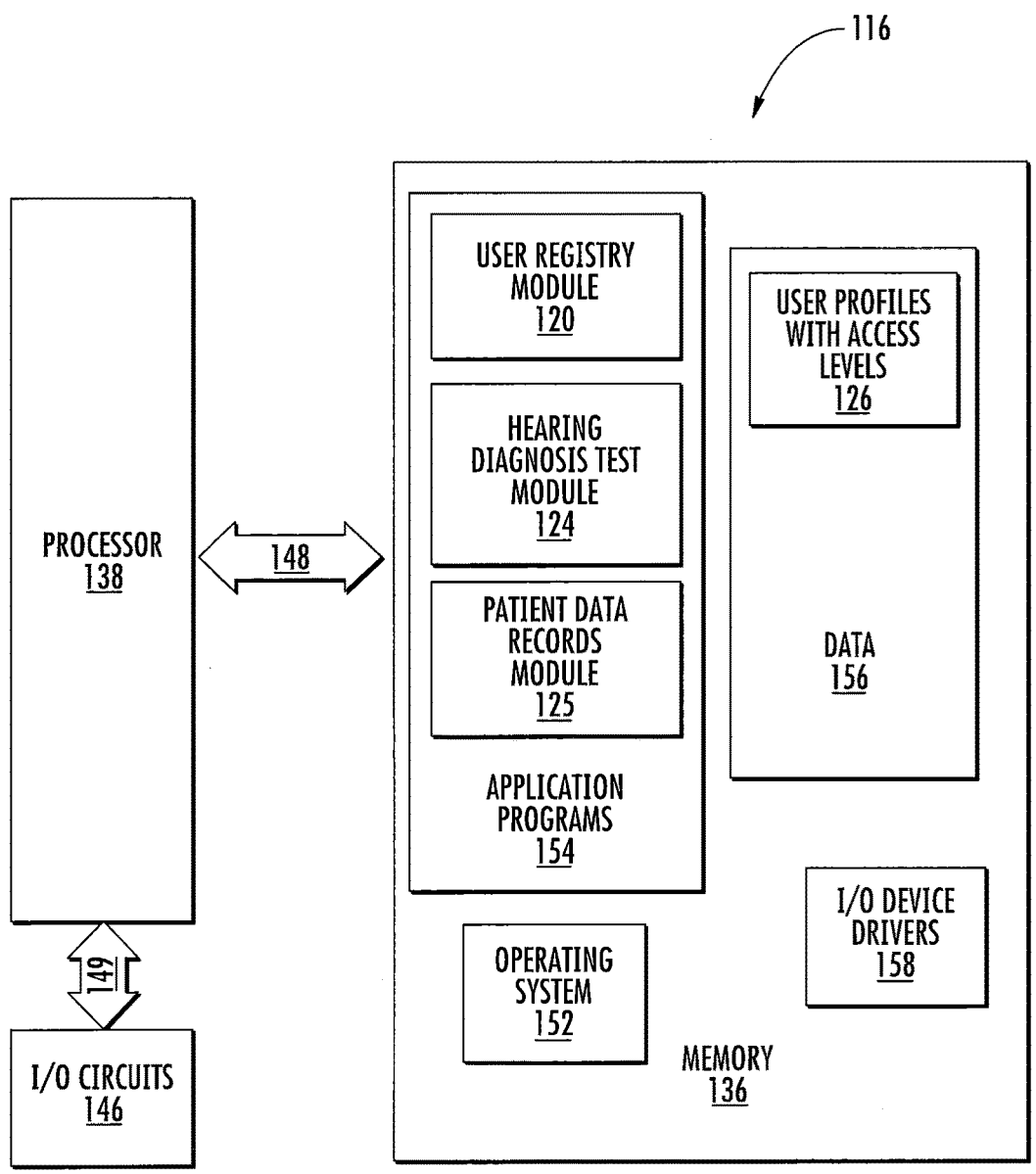
FIG. 12A is a block diagram of a data processing system according to embodiments of the present invention.

FIG. 12A illustrates an exemplary data processing system or database environment that may be included in devices operating in accordance with some embodiments of the present invention. As illustrated in FIG. 12A, a data processing system which can be used to carry out or direct operations of the hub and/or web application (e.g., comprising an Administrative Server) includes a processor 138, a memory 136 and input/output circuits 146. The data processing system may be incorporated in, for example, one or more of a personal computer, server, router or the like. The processor 138 communicates with the memory 136 via an address/data bus 148 and communicates with the input/output circuits 146 via an address/data bus 148. The input/output circuits 146 can be used to transfer information between the memory (memory and/or storage media) 136 and another computer system or a network using, for example, an Internet protocol (IP) connection. These components may be conventional components such as those used in many conventional data processing systems, which may be configured to operate as described herein.

In particular, the processor 138 can be commercially available or custom microprocessor, microcontroller, digital signal processor or the like. The memory 136 may include any memory devices and/or storage media containing the software and data used to implement the functionality circuits or modules used in accordance with embodiments of the present invention. The memory 136 can include, but is not limited to, the following types of devices: cache, ROM, PROM, EPROM, EEPROM, flash memory, SRAM, DRAM and magnetic disk. In some embodiments of the present invention, the memory 136 may be a content addressable memory (CAM).

As further illustrated in FIG. 12A the memory (and/or storage media) 136 may include several categories of software and data used in the data processing system: an operating system 152, application programs 154, input/output device drivers 158, and data 156. The application programs can include a User Registry module 120, a hearing test module 124, a patient record module 125, and the like. The data 156 can include user profiles with defined access levels 126. The user profiles 126 may additionally or alternately include an application program.

Figure 12B:
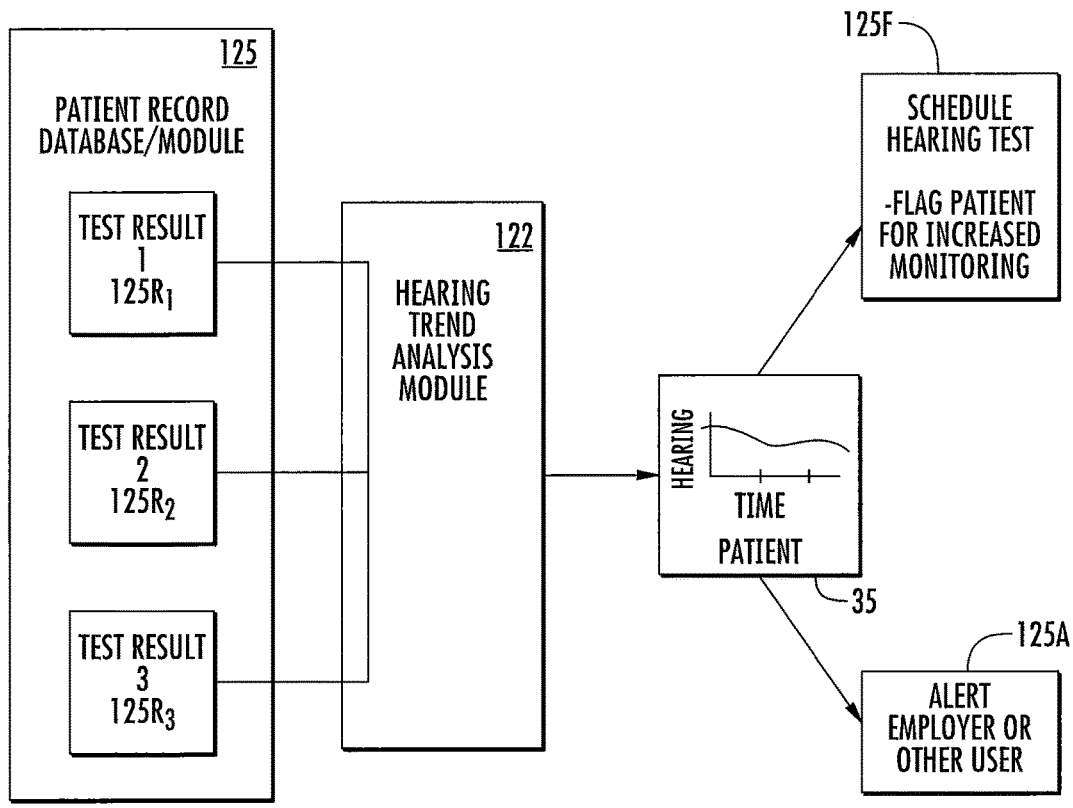
FIG. 12B is a block diagram of another exemplary feature or function of a data processing system according to embodiments of the present invention.

FIG. 12B illustrates the system 10 can include a Hearing Trend Analysis Module 122 (that may be an application program similar to the modules discussed above with respect to FIG. 12A) that can access electronically stored patient records (shown as records 125R1, 125R2 and 125R3) in the patient record database 125 and generate a visual output/display of a graph of hearing test trends. Thus, in some embodiments, the system 10 can be configured to electronically store hearing test results of a patient in a database taken at different past points in time, electronically review the patients past hearing test results (typically upon request by a user), then electronically predict future hearing test results based on the review of past results. A trend can be electronically generated and shown on a display associated with a client 35 (e.g., an audiologist or nurse). The trend can be in graphic form and may indicate a risk of future hearing loss (hearing ability) based at least in part on the past results (change over time or during a specific time interval) and may predict future changes in hearing based on the trend. An increased monitoring period (shorter time interval between tests) can be set for those patients identified as being at increased risk of having a hearing loss. As shown, the system 10 can be configured to generate a "flag" 125F that increases the test frequency or monitoring schedule if that patient is identified as being at risk of hearing loss. The system 10 may also be configured to alert employers via email, postal mail and/or using text messages or other suitable communication protocol 125A to notify an employer (such as Environmental Health and Safety Department personnel or clinical staff) and/or patient-users themselves, of patients having increased risk of hearing loss so that the employer can take corrective action so that those patients can be fitted with hearing loss equipment of different jobs to inhibit further hearing loss. The system 10 may also be configured to notify regulatory agencies such as OHSA (Department of Occupational Health and Safety) of identified cases of hearing loss for employee protection. The notification may be such that any patient identifier data is removed from any such notice to meet HIPPA guidelines.

As will be appreciated by those of skill in the art, the operating system 152 may be any operating system suitable for use with a data processing system, such as IBM®, OS/2®, AIX® or zOS® operating systems or Microsoft® Windows® operating systems, Unix or Linux™. IBM, OS/2, AIX and zOS are trademarks of International Business Machines Corporation in the United States, other countries, or both while Linux is a trademark of Linus Torvalds in the United States, other countries, or both. Microsoft and Windows are trademarks of Microsoft Corporation in the United States, other countries, or both. The input/output device drivers 158 typically include software routines accessed through the operating system 152 by the application programs 154 to communicate with devices such as the input/output circuits 146 and certain memory 136 components. The application programs 154 are illustrative of the programs that implement various features of the circuits and modules according to some embodiments of the present invention. Finally, the data 156 represents the static and dynamic data used by the application programs 154, the operating system 152, the input/output device drivers 158 and other software programs that may reside in the memory 136.

While the present invention is illustrated with reference to the application programs 120, 124, 125 in FIG. 12A (and 122 in FIG. 12B) as will be appreciated by those of skill in the art, other configurations fall within the scope of the present invention. For example, rather than being application programs 154 these circuits and modules may also be incorporated into the operating system 152 or other such logical division of the data processing system. Furthermore, while the application programs 120, 124, 125 (122) are illustrated as modules in a single data processing system, as will be appreciated by those of skill in the art, such functionality may be distributed across one or more data processing systems. Thus, the present invention should not be construed as limited to the configurations illustrated in FIGS. 12A, 12B but may be provided by other arrangements and/or divisions of functions between data processing systems. For example, although FIGS. 12A, 12B are illustrated as having various circuits and modules, one or more of these circuits or modules may be combined without departing from the scope of the present invention.

Typically, during "on-boarding" or customer set-up, a client 35 is brought into the network or system 10 and assigned one or more privacy levels based on a legal or organizational entitlement to send and/or receive certain types (and/or content) of data. An organization may include one or a plurality of web clients 35, each with one or more different assigned privacy levels. The privacy level can define what data that entity or person associated with that entity can receive, send or access.

As shown in FIG. 8, the server 31 can communicate with a registry 120 that can correlate a subscriber user with a particular privacy level and can act to control communications to inhibit or prevent access to non-authorized or non-entitled data, using, for example, a security directory, participant profiles, and rules. Each subscriber/user or registered participant has an assigned privacy level.

The test adapters 20 and associated audiometer 22 or integrated test adapter 20I can be configured to provide, in a calibrated or controlled manner, hearing assessment signals (speech and non-speech signals) in a plurality of different frequencies (such as 5-10 or more frequencies). In some embodiments, at least 8 different frequencies are evaluated during the test, with frequencies ranging between about 20-20,000 Hz, and more typically between 125-12, 000 Hz. The frequency of the tone will also be output to the user/patient with known intensity levels ranging from about 0 to about 120 dB (sound pressure level), depending on the test frequency. The hearing test, provided by the computer networked system, is able to generate tone presentations which meet ANSI standards, thereby providing, in some embodiments, a web-based testing protocol which meets recognized standardized hearing diagnostic standards.

The audiometer 22 (stand alone or on-board) can include a tone generator an output device and an input device. The output device 60 (FIGS. 6A, 6B) can be a transducer such as a bone conduction oscillators or vibrators, insert earphones (i.e., over-the-ear ("OTE"), in-the-ear ("ITE"), behind-the-ear ("BTE")), or conventional supra-aural earphones or headphones or the test adapters can include several types of output devices for serial use by the patient according to audiologist directions/instructions. In some embodiments, it is anticipated that speakers may also be acceptable output devices.

The tone generator is configured to generate the desired frequency tone at the desired level and transmit the tones to the output device. The tone presentation of the hearing signal generated by the tone generator may be "continuously on" or manipulated to present a "pulse tone." For additional discussion of test signals and audiologist controls/commands and on-board test adapter configurations, see, U.S. Pat. No. 6,916,291, the contents of which are hereby incorporated by reference as if recited in full herein. One example of suitable testing protocols is shown in Table 1.

TABLE 1

Frequency and maximum hearing levels for device

| Frequency | Hearing Levels (dB HL) | |
| --- | --- | --- |
| (Hz) | Air | Bone |
| 125 | 70 | |
| 250 | 90 | 45 |
| 500 | 120 | 60 |
| 1000 | 120 | 70 |
| 2000 | 120 | 70 |
| 3000 | 120 | 70 |
| 4000 | 120 | 60 |
| 6000 | 110 | 50 |
| 8000 | 100 | |
| 12000 | 90 | |

The tone presentation may be adjusted or determined depending on the configuration of the output device in use or the particular testing protocol desired (different output devices may be used at different local patient sites typically depending on (a) the patient and (b) the noise associated with the testing environment). In certain embodiments, the pulse length is presented to the patient such that it does not exceed about 225±35 ms. For air conducted signals, the tone is typically transmitted to the user for at least about 20 ms and such that it is equal to or less than about 50 ms. For bone-conducted signals, the rise or onset time shall be no less than 20 ms. When the tone is terminated, the "fall" time is less than about 20 ms. The duration of the tonal plateau can be presented to the patient such that it is equal to or above about 150 ms.

As shown above in Table 1, the testing protocol can include 10 different frequencies ranging from 125 Hz to 12000 Hz. Additional or lesser frequencies can be used, depending on the applicable test standard, although typically, the test frequencies will be between 20-20,000 Hz. The frequency accuracy for each test signal tone generated can be presented to the patient such that the signal is within about 1% of the indicated tone frequency.

In certain embodiments, the hearing assessment presentation signals can include frequency tones, narrow band noise, broadband noise, recorded noise and speech, as well as live speech. In certain embodiments, the device 20, 22 or 20I may also be configured such that the harmonic distortion of the tone frequencies are able to meet the current ANSI standards; an example of a current standard ANSI-53.6 1996 is listed in Table 2. Thus, in certain embodiments, the maximum level of the harmonics of the test tone relative to the level of the fundamental may be presented so as to not exceed the values given in Table 2 below.

TABLE 2

Maximum permissible harmonic distortion, expressed in percent *

| | Air Conduction | | | | Bone Conduction | | |
|---|---|---|---|---|---|---|---|
| Frequency (Hz) | 125 | 250 | 500-4000 | 6000-16000 | 250 | 500-750 | 1000-5000 |
| Hearing level | 75 | 90 | 110 | 90 | 20 | 50 | 60 |
| Second harmonic | 2 | 2 | 2 | 2 | 5 | 5 | 5 |
| Third harmonic | 2 | 2 | 2 | | 2 | 2 | 2 |
| Fourth & each higher harmonic | .3 | .3 | .3 | | 2 | 2 | 2 |
| All subharmonics | | .3 | .3 | .3 | | | |
| Total harmonic | 2.5 | 2.5 | 2.5 | 2.5 | 5.5 | 5.5 | 5.5 |

* ANSI-S3.6 1996

In operation, the desired hearing tone presentation is transmitted to the output device and to the patient. In response, the patient can indicate a response to the tone to the input device. The input device can be a voice activated or speech recognition input microphone, or a physical input port such as a keypad, button, screen-contact software switch, or physical switch. As noted above, in certain embodiments, the input device can be (or include) a video camera which is video linked to the test administration site so that the clinician can visually monitor the patient's response during the test. Further, two individually operable input devices can be employed: one for use when the patient acknowledges a tone to the right ear and one for when the patient acknowledges hearing from the left ear. It will be appreciated that, in some embodiments, the input device may be on the output transducer headset itself as an alternative to the housing body of the device. The test device 20, 22 and/or 20I may, in some embodiments, include or communicate with a microphone to measure the ambient or environmental noise within the testing room or locale, at the patient site. This embodiment can allow the system to assure that the test complies with appropriate standards, such as ANSI S3.1-1999. This standard specifies the maximum permissible ambient noise levels (MPANL) allowed in a room for audiometric threshold assessment. In certain embodiments, the microphone can be configured to measure or detect sound pressure levels or noise in the range of between about 20 Hz to 20 kHz, and may, in some embodiments, detect sound pressure levels at octave intervals 125 to 8,000 Hz or up to 12,000 or greater Hz. The microphone may operate prior to initiation of the testing procedure to determine what the noise or sound level is and if a particular type of output device should be employed (such as whether supra-aural or insert earphones are appropriate to meet the applicable standard).

Sound Level Measurement of Ambient Noise

TABLE 3

Octave band ears covered maximum permissible ambient noise levels

| Octave Band Intervals (Hz) | Supra-aural Earphones | Insert Earphones |
|---|---|---|
| 125 | 39.0 | 67.0 |
| 250 | 25.0 | 53.0 |
| 500 | 21.0 | 50.0 |
| 1000 | 26.0 | 47.0 |
| 2000 | 34.0 | 49.0 |
| 4000 | 37.0 | 50.0 |
| 8000 | 37.0 | 56.0 |

Values are in dB re: 20 uPa to nearest 0.5 dB

In other embodiments, a passive biotelemetry reading of the structure/operation of the ear (i.e., middle ear analysis, cochlea hair cell response, and the like) can be obtained. This measurement or reading can be administered in addition to (or separately from) the tone hearing test protocol. The biotelemetry sensor can be incorporated into the transducer output device 60 (FIGS. 6A, 6B) or can be an additional component. In operation, an operator at the test administration site can activate the local biotelemetry sensor in the ear of the subject and the associated measurement can be passively obtained (without requiring the subject to verbally or visually communicate). The measurement can be relayed to the test administration site via the communication link to the computer network 10. The biotelemetry methods/systems can acquire multiple data sets and transmit them through the computer network to allow a remotely located clinician to generate a biotelemetry analysis of the auditory system of the patient. The multiple data sets can include data corresponding to auditory evoked potentials from clicks, tonal or speech stimuli, otoacoustic emissions from either distortion-product and/or transient approaches, middle-ear compliance (achieved from either single or multiple frequency stimulation and pressure) and/or acoustic reflex response. Thus, for example, the system can be configured to provide the remote web-gathering of auditory evoked potentials. The local biotelemetry sensor may be activated/controlled by the remote site in a manner that allows for adjustment during the evaluation and/or measurement such that the data is relayed to the remote/test administration site in substantially "real-time" or at certain points in time during administration of the test. Embodiments of systems and methods related to web-based acquisition and analysis of transient and distortion product otoacoustic emissions and middle ear testing will be described further below.

Figure 13A:
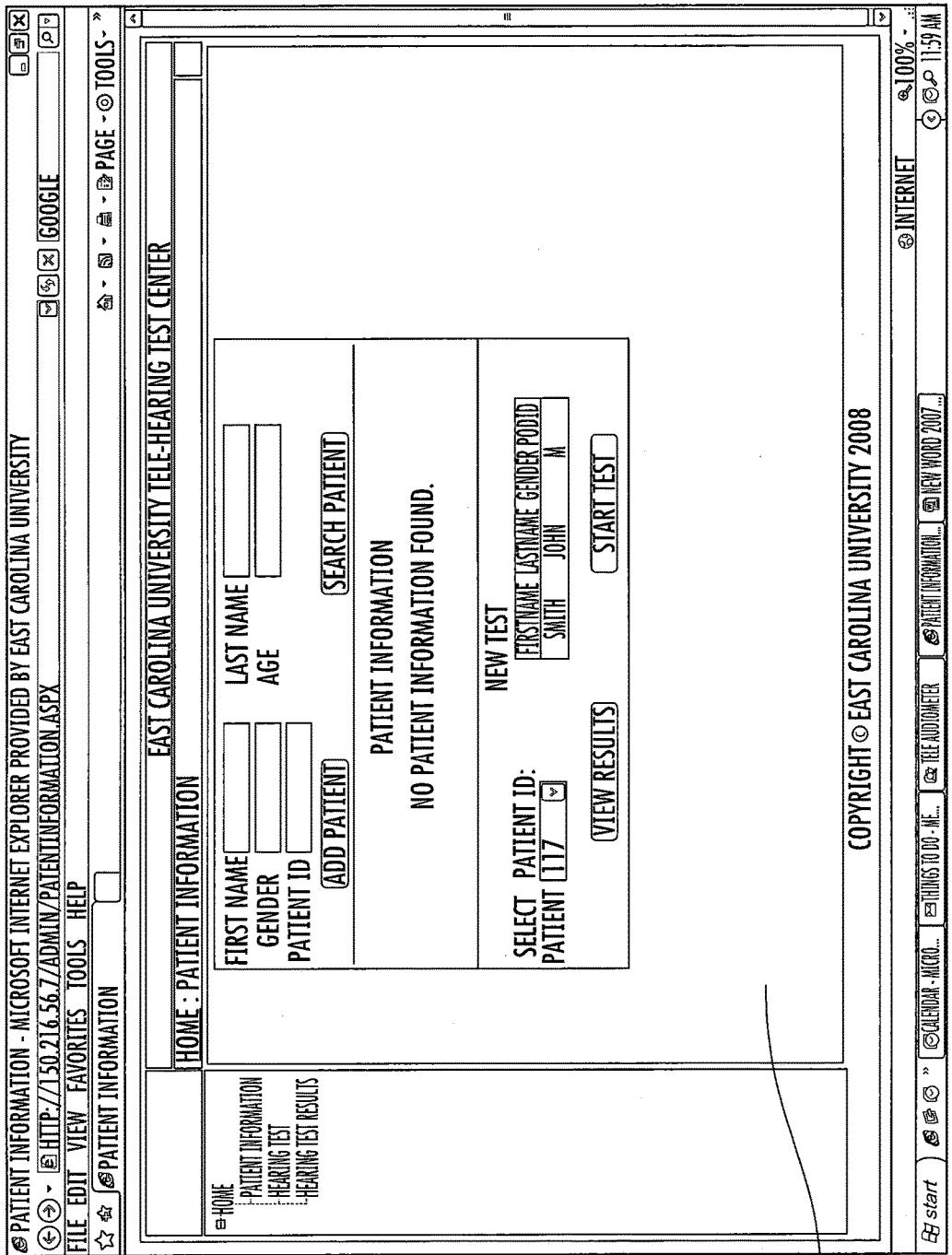
Figure 13B:
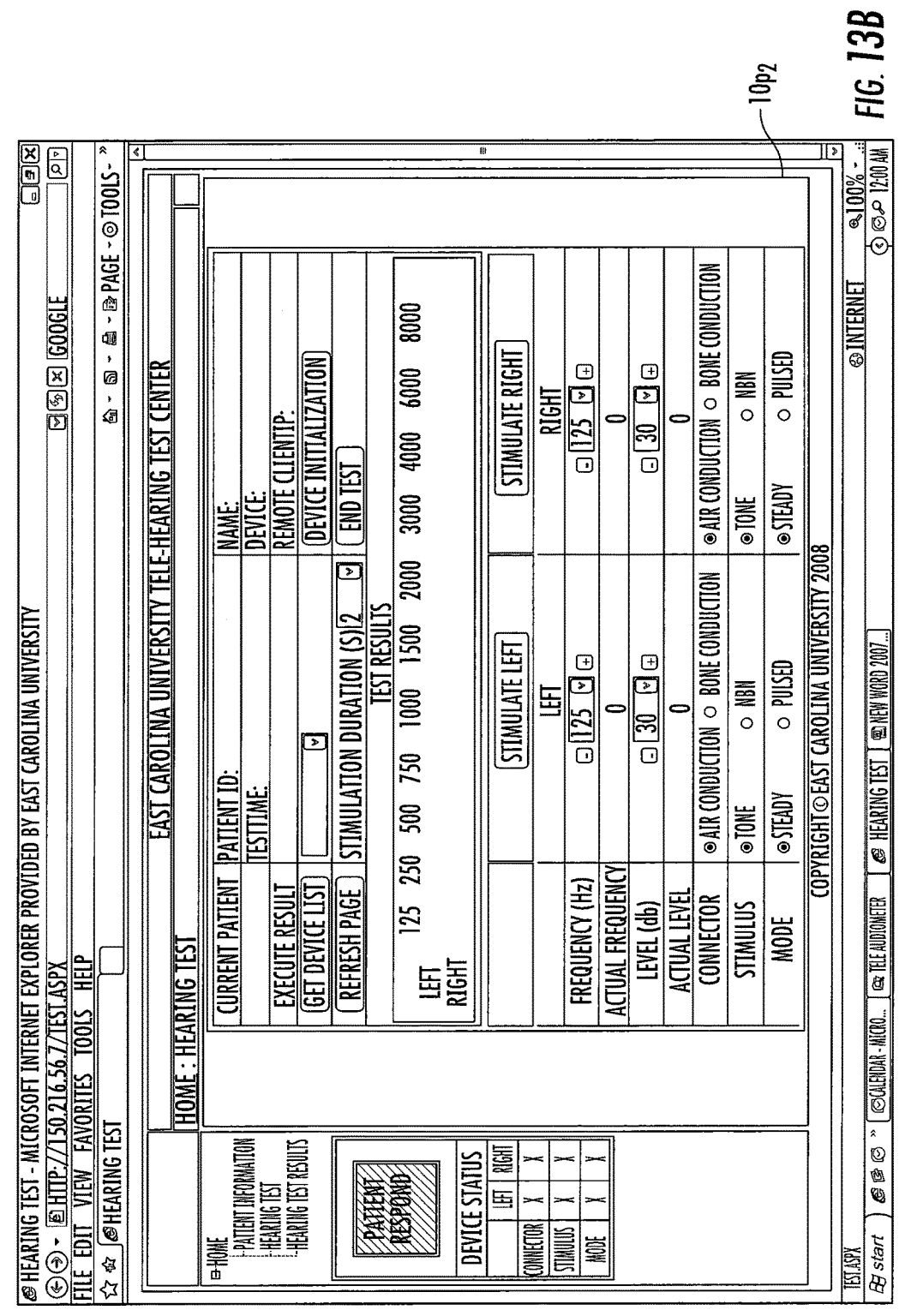
Figure 13C:
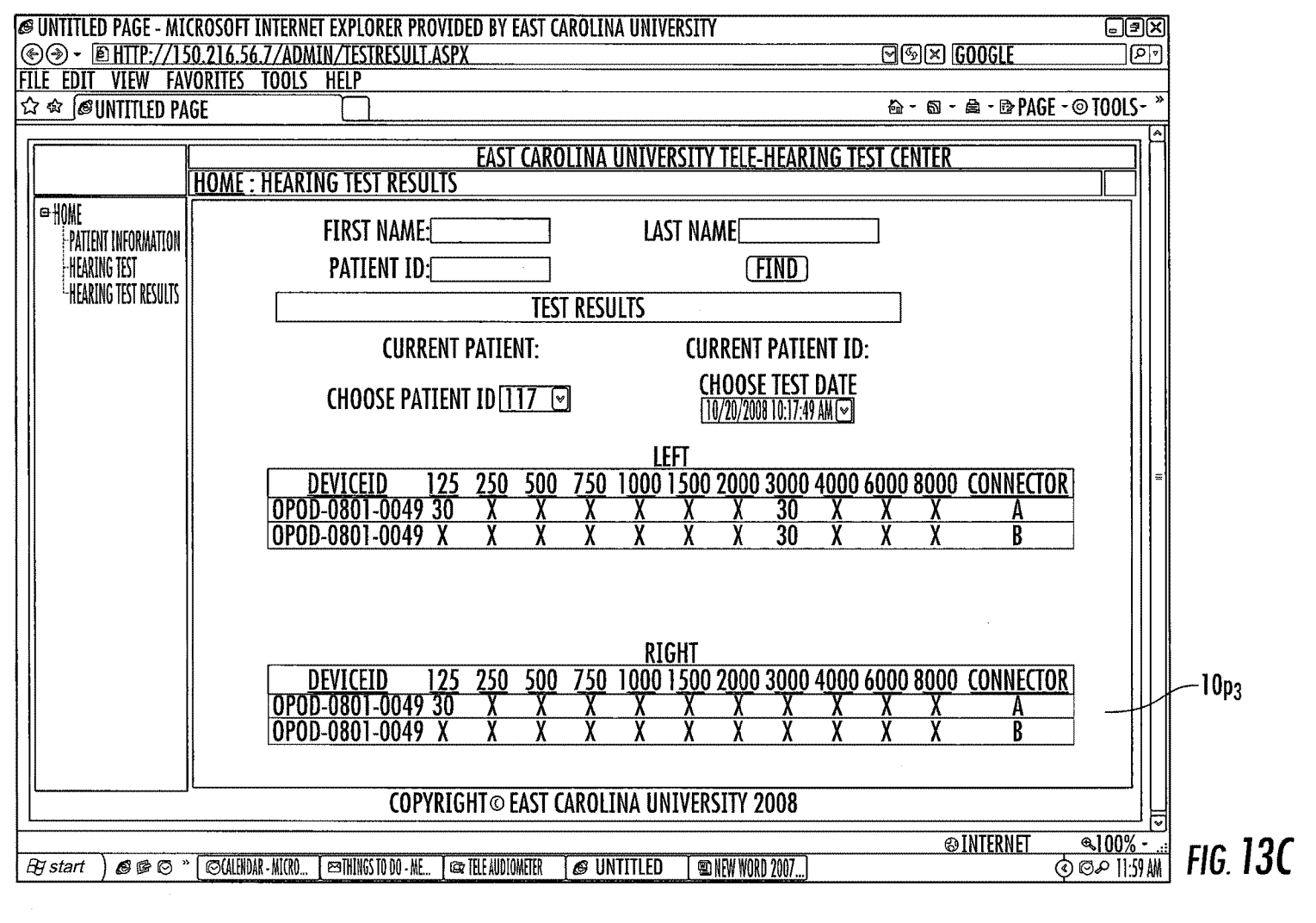

FIGS. 13A-13C illustrate exemplary web pages $10p_1$-$10p_3$ associated with an audiologist user 40. FIG. 13A illustrates a Patient Information web page with the patient information, patient ID, and Test Adapter Device ID. The user 40 can start a new test or view results of a test. Based on the selection of the "start test" in the NEW TEST section of web page $10p_1$, FIG. 13B displays the second web page $10p_2$ with control selections and actions for the audiologist. The interface on the left with "PATIENT RESPOND" indicates that it is waiting for a patient to respond to the signal and indicates the status of the device (Left, Right, connector, stimulus and mode). The connector type refers to air conduction or bone conduction. The stimulus selection includes tone and NBN (narrow band noise) and the mode refers to steady and pulsed. The web page $10p_2$ also illustrates a duration selection input and a device initialization input as well as an END TEST selection. FIG. 13C illustrates a third web page $10p_3$ that provides the hearing test results with the audiometer and/or test adapter identification and Left and Right hearing results by connector type (A or B).

Figure 2:
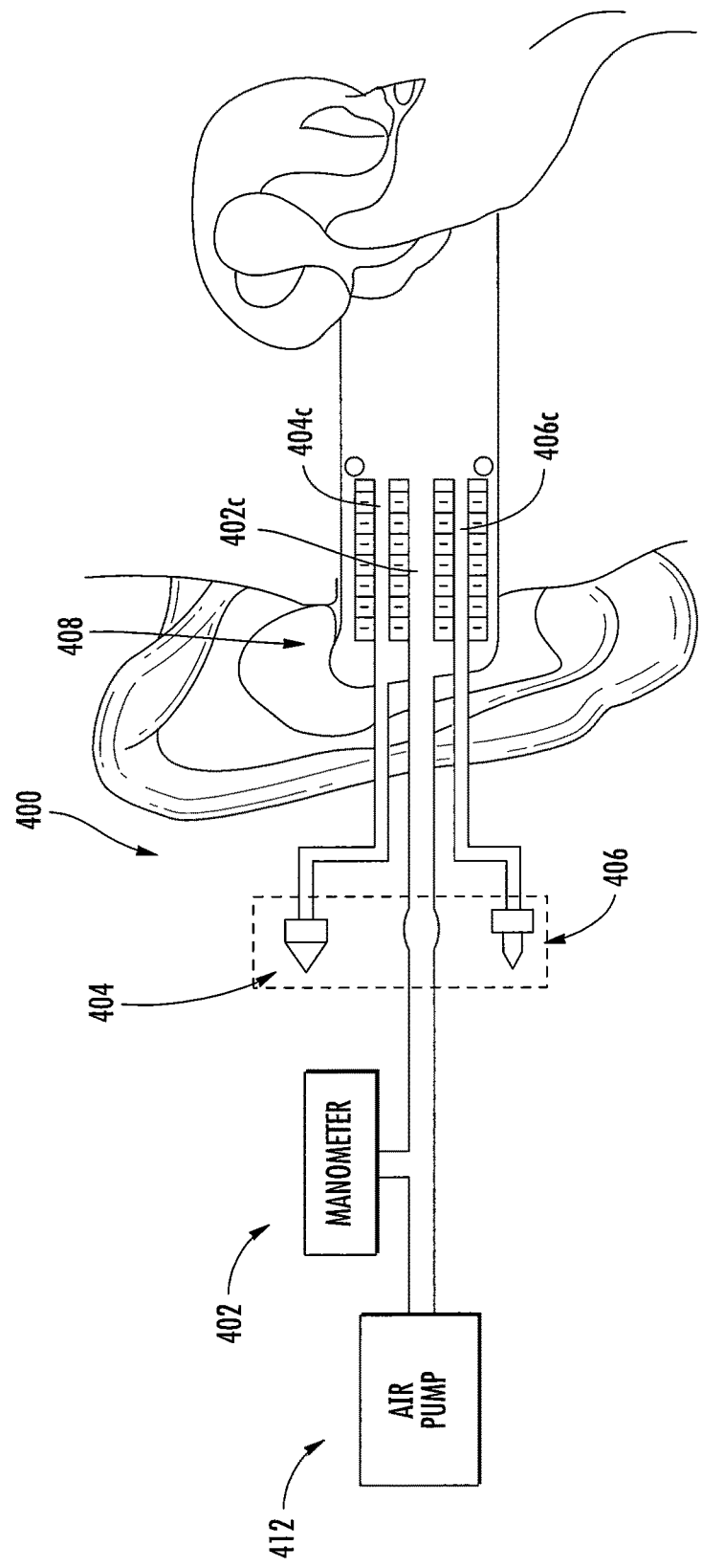
FIG. 2 is a schematic illustration of the hearing probe of FIG. 1 inserted in the ear canal of a patient.

The measurement of otoacoustic emissions, tympanometry and acoustic reflexes can be achieved in the same hardware probe unit. A probe or probe unit 400 according to some embodiments is illustrated in FIGS. 1 and 2. The unit 400 includes a manometer 402 (used during tympanometry and reflexes), a sound signal source such as speaker 404, and a microphone 406. These components are all included in the probe unit 400 which is inserted into the external ear canal 408 of a patient for secure fitting to seal off the canal from the outside environment.

A primary purpose of otoacoustic emission (OAE) tests is to determine cochlear status, specifically hair cell function. This information can be used to (1) screen hearing (particularly in neonates, infants, or individuals with developmental disabilities), (2) partially estimate hearing sensitivity within a limited range, (3) differentiate between the sensory and neural components of sensorineural hearing loss, and (4) test for functional (feigned) hearing loss. The information can be obtained from patients who are sleeping or even comatose because no behavioral response is required.

The normal cochlea does not just receive sound; it also produces low-intensity sounds called OAEs. These sounds are produced specifically by the cochlea and, most probably, by the cochlear outer hair cells as they expand and contract.

The probe 400 includes a soft flexible tip 410 and is inserted in the ear canal 408 to obtain a seal. Different probes are typically used for neonates and adults; the probes are calibrated differently because of the significant difference in ear canal volume. The smaller ear canal results in a higher effective sound pressure level (SPL), thus a different probe is used to correct for the difference.

Multiple responses may be averaged. All OAEs are analyzed relative to the noise floor; therefore, reduction of physiologic and acoustic ambient noise is critical for good recordings. Because no behavioral response is required, OAEs can be obtained even from patients who are comatose. For a quiet and cooperative patient, recordings usually require less than a few minutes per ear. For an uncooperative or noisy patient, recordings may take significantly longer or may be impossible to obtain for a given test.

Various types of emissions will now be described. Spontaneous otoacoustic emissions (SOAEs) are non-evoked responses that are usually measured in narrow bands (<30 Hz bandwidth) of frequencies recorded in the external ear canal. No stimulus is required. Multiple recordings are obtained to ensure replicability and to distinguish the response from the noise floor. SOAE recordings usually span the 500-Hz to 7000-Hz frequency range.

For transient otoacoustic emissions (TOAEs), clicks are the most commonly used stimuli, although tone-burst stimuli may be used. Most commonly, 80- to 85-dB SPL stimuli are used clinically. The stimulation rate is less than 60 stimuli per second. TOAEs are generally recorded in the time domain over approximately 20 milliseconds. Alternating responses are stored in alternating computer memory banks. Data that correlate between the two memory banks are considered a response. Data that do not correlate are considered noise. When present, TOAEs generally occur at frequencies of 500-4000 Hz. Data in the time domain then are converted to the frequency domain, usually in octave band analysis.

For distortion product otoacoustic emissions (DPOAEs), stimuli consist of 2 pure tones at 2 frequencies (i.e., f1 and f2, with f2>f1) and two intensity levels (i.e., L1, L2). The relationship between L1-L2 and f1-f2 dictates the frequency response. An f1/f2 ratio yields the greatest DPOAEs at 1.2 for low and high frequencies and at 1.3 for medium frequencies. To yield an optimal response, intensities may be set so that L1 equals or exceeds L2. Lowering the absolute intensity of the stimulus renders the DPOAEs more sensitive to abnormality. A setting of 65/55 dB SPL L1/L2 is frequently used. Responses are usually most robust and recorded at the emitted frequency of 2 f1-f2; however, they generally are charted according to f2 because that region approximates the cochlear frequency region generating the response.

Important factors for obtaining otoacoustic emissions include an unobstructed outer ear canal and a seal of the ear canal with the probe. Optimal positioning of the probe can also be important.

Tympanometry and acoustic reflexes involve the use of a probe inserted into the ear canal with a tight seal so that air does not leak out or at least is restricted. The assumption behind tympanometry is that in order for the middle ear to be most efficient at passing incoming sounds through it, air pressure should be even on both sides of the tympanic membrane (TM).

The probe 400 has a channel 404c that communicates with the speaker 404, a channel 406c that communicates with the microphone 406, a channel 402c that allows a change in air pressure in the ear canal (e.g., using the manometer 402 and a pump 412 in communication with the manometer 402). During the air pressure changes, a steady low-frequency tone at, for example, 70 dB sound pressure level (SPL) is presented through the probe speaker 404, and the probe microphone 406 picks up any sound that bounces back off from the TM. If the least amount of sound bounces back off the TM when the air pressure in the outer ear canal is at regular room air pressure, this means the air pressure behind the TM is the same. In this way, tympanometry measurement in the outer ear canal provides information about the middle ear air pressure behind the TM.

Tympanometry typically uses a low frequency tone because, with tympanometry, the compliance of the middle ear is tested by measuring the amount of low-frequency tone reflecting off the stiff middle ear as a function of air pressure changes. Compliance is the opposite or inverse of stiffness. Tympanometry uses a low-frequency tone because the middle ear is a "stiffness dominated system." The middle ear system, which involves the TM and ossicular chain, is always relatively stiff, but it is least stiff when the air pressure is even on both sides of the TM. The middle ear ossicles are tiny and therefore do not have much mass. Stiffness is therefore the main source of opposition to the passage of sound through the middle ear. Stiffness opposes the passage of low frequencies and resonates with high frequencies, while mass opposes the passage of high frequencies and resonates with low frequencies. A low frequency tone is used so that some sound will bounce off from the TM, even when the middle ear is least stiff.

In the normal situation, the air pressures inside the outer ear canal and the middle ear space are both at regular room air pressure. When the low frequency tone is presented at 70 dB SPL, some of it will pass through the stiff middle ear system, but because the middle ear is a stiffness dominated system, some of it will bounce back off the TM. With positive or negative air pressure in the outer ear canal however, the air pressure is made to be different from that inside the middle ear space, and this makes the normally stiff middle ear system become stiffer yet. In these situations, even more sound bounces off the TM and less goes through it. In other words, with uneven air pressure on both sides of the TM, the middle ear is made temporarily more stiff than it usually is and therefore, less efficient.

The test adapter 20 or 20I described above can be configured to operate in conjunction with the probe 400 (e.g., instead of or in addition to operating in conjunction with an audiometer). For example, the adapter 20 or 20I can convert data from the probe 400 (which are in turn sent to the audiologist over the network 100) and also convert operational commands from an audiologist in a format that can be accepted by the probe 400. Therefore, the audiologist may be able to operate the probe 400 remotely, including controlling the speaker 404 to produce a tone and controlling the manometer 402 and/or pump 412 to control the pressure inside the ear of the patient. The audiologist may also remotely receive test results as measured by the microphone 406 of the probe 400.

The test adapter 20 or 20I may also be used to determine if the probe 400 has been inserted in the ear to have a proper seal (e.g., to confirm that the probe is sealingly engaged in the patient's ear so that no air can enter or exit the air past the probe). For example, the manometer 402 may be used to determine the pressure in the ear. In some embodiments, the pump 412 may be used to increase a pressure in the ear, and the manometer 402 may be used to confirm that the pressure remains the same over a predetermined period of time, thereby ensuring an adequate seal. The test adapter 20 or 20I may communicate to the remote audiologist whether or not the probe 400 has been inserted with a proper seal.

Figure 3:
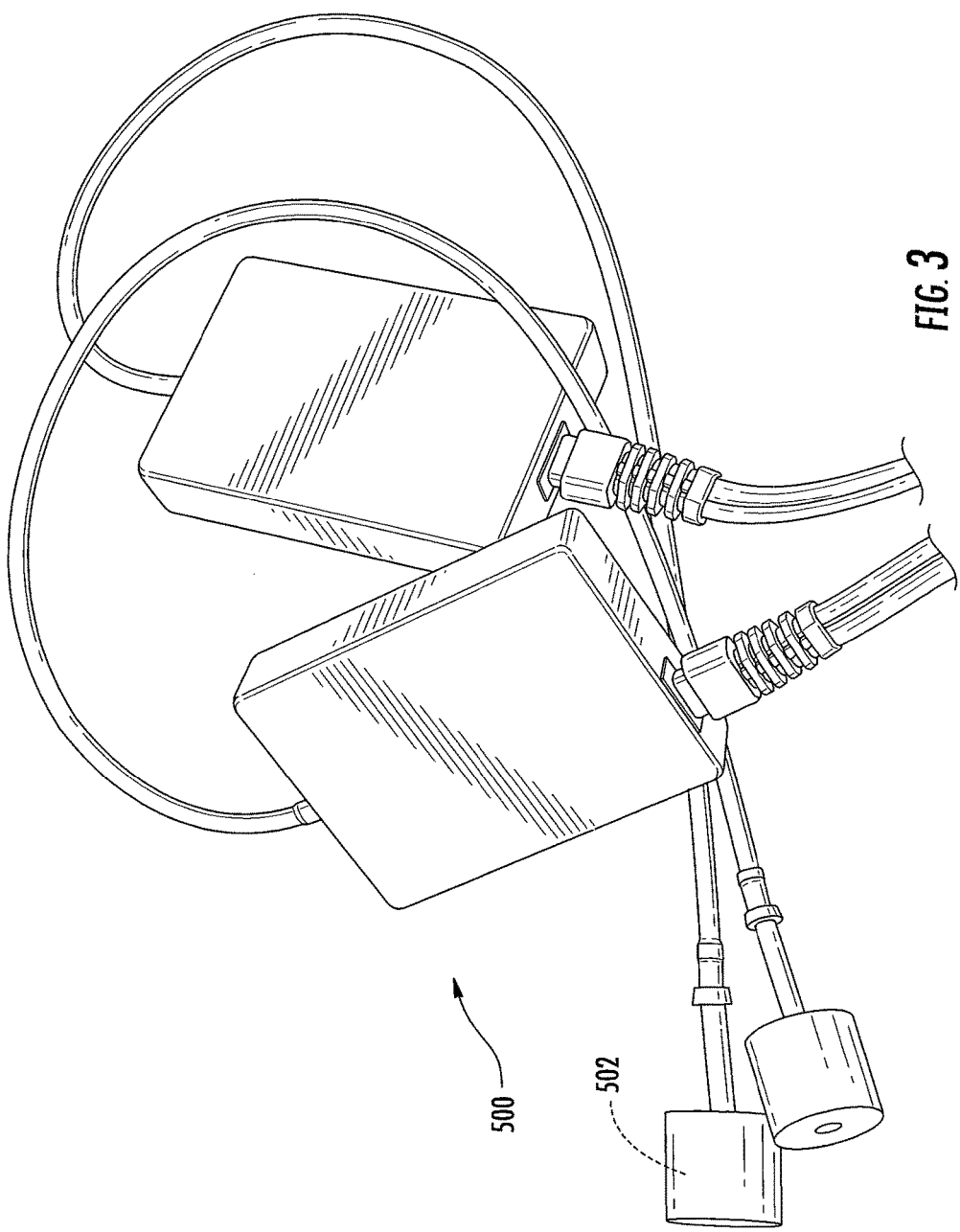
FIG. 3 is a perspective view of hearing test probes that are configured to be inserted in the ear canals of a patient according to embodiments of the present invention.
Figure 4:
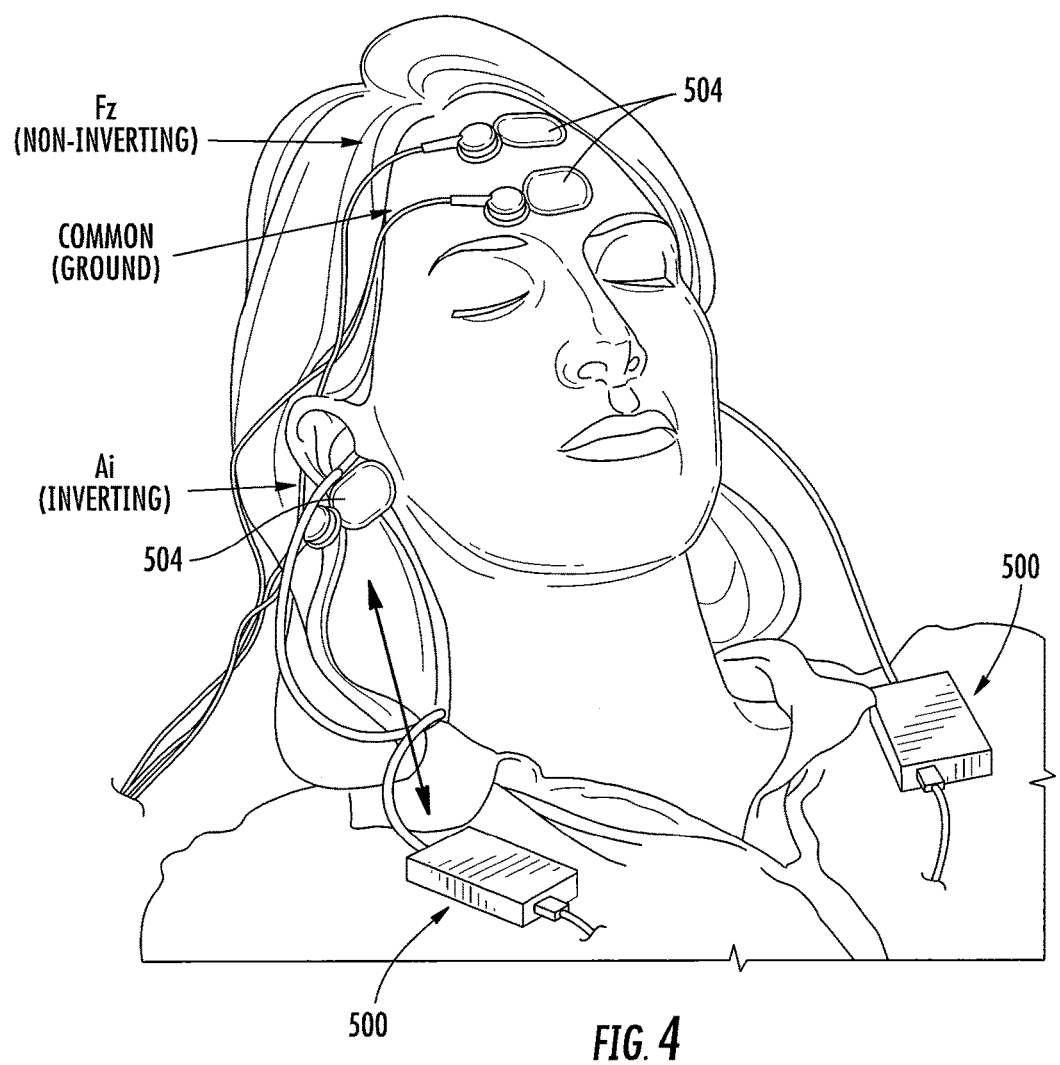
FIG. 4 is a perspective view of the hearing probes of FIG. 3 inserted in the ear canals of a patient and electrodes placed on the patient's face and/or head for use with auditory brainstem response audiometry according to embodiments of the present invention.
Figure 5:
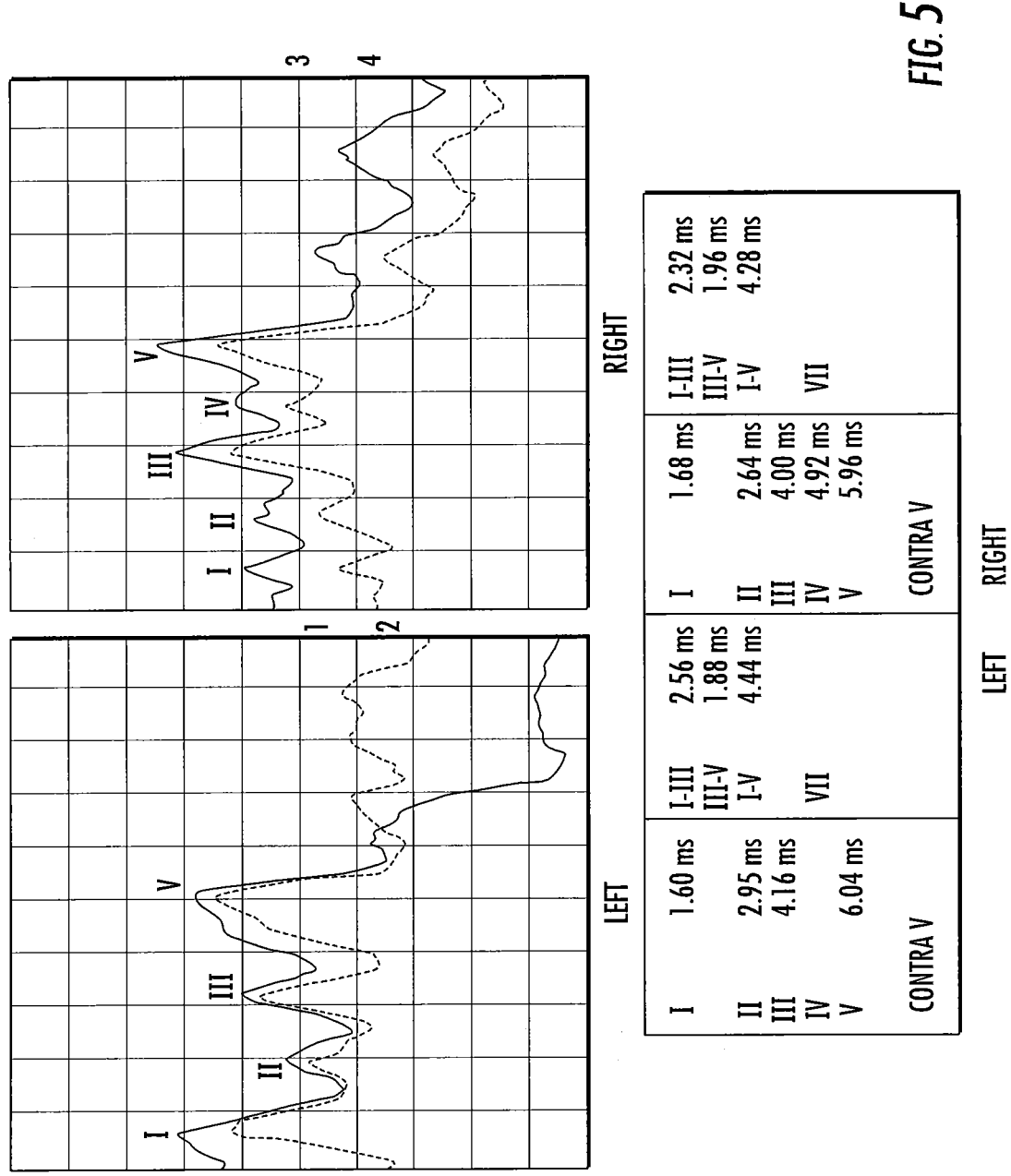
FIG. 5 is a chart illustrating auditory brainstem response waveform response using the hearing probes and electrodes of FIG. 4.

Auditory brainstem response (ABR) audiometry is a neurologic test of auditory brainstem function in response to auditory (click) stimuli. Referring to FIGS. 3 and 4, ABR audiometry refers to an evoked potential generated by a brief click or tone pip transmitted from an acoustic transducer or speaker 502 in a headphone or insert testing probe 500. The probe 500 may be the same or similar to the ear probe 400 described above or, alternatively, may be an on-the-ear headphone. An elicited waveform response is measured by surface electrodes 504 typically placed at the vertex of the scalp and ear lobes. Referring to FIG. 5, the amplitude (e.g., microvoltage) of the signal may be averaged and charted against the time (e.g., in milliseconds). The waveform peaks are labeled I-V. These waveforms normally occur within a 10-millisecond time period after a click stimulus presented at high intensities (70-90 dB normal hearing level [nHL]).

The waves following the ABR, up to roughly 80 ms, are collectively known as the middle-latency response (MLR). Although responses in this time frame are less mappable to specific neural generators than the earlier ABR waves, the thalamus and cortex are involved. As ABR requires a high degree of neural synchrony, individuals with certain neurological disorders may exhibit absent ABRs despite normal hearing. Thus, MLR can be useful in assessing hearing sensitivity. For this same reason, a lack of sufficient synchrony in response to low frequency signals often makes MLR superior to ABR in assessing low-frequency hearing. Two caveats in MLR as a hearing measure is that it does not reach its mature morphology until adolescence, and in children, there is a strong influence of sleep state.

Late-latency (>80 ms) auditory evoked potentials (AEPs) are cortical in origin and are much larger and lower in frequency than early and middle-latency potentials. Highly dependent upon stimulus type, recording location, recording technique, patient age and state, the late-latency responses may differ dramatically in morphology and timing and may overlap one another. Categorization of responses into two broad types, exogenous and endogenous, is useful in describing these late potentials. Exogenous responses, which also describe early and middle-latency potentials, are more-or-less obligatory responses to a sound. Endogenous responses typically require a stimulus manipulation or the performance of a task by the patient.

Auditory brainstem response (ABR) audiometry is considered an effective screening tool in the evaluation of suspected retrocochlear pathology such as an acoustic neuroma or vestibular schwannoma. However, an abnormal ABR finding suggestive of retrocochlear pathology indicates the need for MRI of the cerebellopontine angle.

In addition to retrocochlear pathologies, many factors may influence ABR results, including the degree of sensorineural hearing loss, asymmetry of hearing loss, test parameters, and other patient factors. These influences should be factored in when performing and analyzing an ABR result.

Findings suggestive of retrocochlear pathology may include any 1 or more of the following:
  Absolute latency interaural difference wave V—Prolonged
  I-V interpeak interval interaural difference—Prolonged
  Absolute latency of wave V—Prolonged as compared with normative data
  Absolute latencies and interpeak intervals latencies I-III, I-V, III-V—Prolonged as compared with normative data
  Absent auditory brainstem response in the involved ear In general, ABR exhibits a sensitivity of over 90% and a specificity of approximately 70-90%.

Although traditional ABR measures decrease in sensitivity as a factor of tumor size, recent studies have shown that by using a new stacked derived-band ABR that measures amplitude, very small tumors may be detected more accurately. This new technique, combined with traditional ABR audiometry, may soon make possible the detection of very small tumors with accuracy approaching 100% using ABR audiometry.

Auditory brainstem response (ABR) technology is used in testing newborns. Approximately 1 of every 1000 children is born deaf; many more are born with less severe degrees of hearing impairment, while others may acquire hearing loss during early childhood.

Historically, only infants who met one or more criteria on the high-risk register were tested. Universal hearing screening has been recommended because about 50% of the infants later identified with hearing loss are not tested when neonatal hearing screening is restricted to high-risk groups. Recently, hospitals across the United States have been implementing universal newborn hearing screening programs. These programs are possible because of the combination of technological advances in ABR and otoacoustic emissions (OAE) testing methods and equipment availability, which enables accurate and cost-effective evaluation of hearing in newborns.

When used as a threshold measure to screen for normal hearing, each ear may be evaluated independently, with a stimulus presented at an intensity level of 35-40 dB nHL. Click-evoked ABR is highly correlated with hearing sensitivity in the frequency range from 1000-4000 Hz. ABRs test for the presence or absence of wave V at soft stimulus levels. No operator interpretation is required. ABR can be used on the ward and during oxygen therapy without disturbance from ambient noise.

ABRs may be used to detect auditory neuropathy or neural conduction disorders in newborns. Because ABRs are reflective of auditory nerve and brainstem function, these infants can have an abnormal ABR screening result even when peripheral hearing is normal.

Infants that do not pass the newborn hearing screenings do not necessarily have hearing problems. When hearing loss is suspected because of an abnormal ABR screening result, a follow-up diagnostic threshold ABR test is scheduled to determine frequency-specific hearing status. Estimation of hearing at specific frequencies may be obtained through use of brief tone stimulation, such as a tone burst.

Auditory brainstem response (ABR) audiometry has a wide range of clinical applications, including screening for retrocochlear pathology, universal newborn hearing screening, and intraoperative monitoring. Additional applications include ICU monitoring, frequency-specific estimation of auditory sensitivity, and diagnostic information regarding suspected demyelinating disorders (e.g., multiple sclerosis). As technology continues to evolve, ABR will likely provide more qualitative and quantitative information regarding the function of the auditory nerve and brainstem pathways involved in hearing.

Referring to FIGS. 3, 4, 6A and 6B, the test adapter 20 or 20I described above can be configured to operate in conjunction with the earphone or probe 500 (e.g., instead of or in addition to operating in conjunction with an audiometer). Therefore, the audiologist may be able to operate the earphone or probe 500 remotely, including controlling the earphone or probe 500 to produce a click. The audiologist may also remotely receive test results as measured by the electrodes 504.

In summary, particular aspects of the invention provide a distributed telehearing system that can be configured so that maintenance, support, and management can be physically and/or logically separate from clinical services and may use any suitable architecture such as, for example, browser-server or client-server.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses, where used, are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A medical hearing testing method comprising:
    inserting a first test probe that is coupled to a first hearing test adapter into an ear of a first patient at a first patient site, wherein the first hearing test adapter comprises a first integrated audiometer and a first communication circuit configured to convert a first control operation into a first operational command for the first integrated audiometer and/or the first test probe, wherein the first control operation is received from a network protocol of an electronic network;
    inserting a second test probe that is coupled to a second hearing test adapter into an ear of a second patient at a second patient site, different from the first patient site, wherein the second hearing test adapter comprises a second integrated audiometer and a second communication circuit configured to convert a second control operation into a second operational command for the second integrated audiometer and/or the second test probe, wherein the second control operation is received from the network protocol of the electronic network;
    electronically establishing a first session between a first user and a web portal and providing a first user interface that is customized based on first access permissions for the first user over the web portal, wherein the first access permissions permit the first user to control the first hearing test adapter and the second hearing test adapter using the first user interface;
    electronically establishing a second session between a second user and the web portal and providing a second user interface, different from the first user interface, that is customized based on second access permissions for the second user over the web portal;
    electronically establishing a third session between a third user and the web portal and providing a third user interface over the web portal, different from the first user interface, that is customized based on third access permissions for the third user;
    controlling first and second concurrent hearing tests at the first and second patient sites, respectively, by electronically transmitting, by the first user, the first control operation to the first hearing test adapter and the second control operation to the second hearing test adapter;
    converting, by the first communication circuit, the first control operation into the first operational command, wherein the first operational command controls an operation of the first integrated audiometer and/or the first test probe;
    converting, by the second communication circuit, the second control operation into the second operational command, wherein the second operational command controls an operation of the second integrated audiometer and/or the second test probe; and
    transmitting, to the first user via the web portal, a first response from the first hearing test adapter and a second response from the second hearing test adapter responsive to the first operational command and the second operational command, respectively.

2. The method of claim 1, wherein the first operational command controls the operation of the first test probe to alter an ear canal pressure of the first patient.

3. The method of claim 2, wherein altering the ear canal pressure of the first patient comprises increasing a pressure of the ear canal of the first patient with respect to an atmospheric pressure.

4. The method of claim 3, wherein altering the ear canal pressure of the first patient comprises remotely electronically controlling operation of a manometer and/or a pump associated with the first test probe.

5. The method of claim 2, wherein the first operational command controls the operation of the first test probe to output a tone using a speaker associated with the first test probe during and/or after altering the ear canal pressure of the first patient.

6. The method of claim 1, wherein the operational command controls the operation of the first test probe to output a tone using a speaker associated with the first test probe and to measure sound that reflects off a tympanic membrane of the first patient's ear using a microphone associated with the first test probe.

7. The method of claim 1, wherein the operational command is used to determine if the first test probe is sealingly engaged with the first patient's ear.

8. The method of claim 1 further comprising:
    receiving the first response to the first operational command from the first hearing test adapter over the electronic network at the web portal; and
    electronically storing the first response in a storage medium coupled to the web portal.

9. The method of claim 8, wherein the first response is received at the web portal on a first date, and
wherein the method further comprises:
receiving a third response to a third operational command from the first hearing test adapter over the electronic network at the web portal on a second date; and
analyzing the first response and the third response to develop a hearing trend for the first patient.

10. The method of claim 9 further comprising:
altering a frequency of testing for the first patient responsive to the hearing trend.

11. The method of claim 1, wherein the first operational command controls the operation of the first integrated audiometer and/or the first test probe to alter an audio frequency of a tone transmitted by the first test probe into the ear of the first patient.

12. The method of claim 1 further comprising:
transmitting multimedia communications between the first user and the first patient over the electronic network during the first hearing test, wherein transmitting multimedia communications comprises transmitting speech of the first patient during the test first hearing test.

13. A medical hearing test method comprising:
(a) receiving a hearing test adapter from a plurality of hearing test adapters shipped to a plurality of different patient sites;
(b) receiving first device identification data uniquely identifying a first hearing test adapter at a first patient site from among the plurality of different patient sites;
(c) transmitting the first device identification data from the first hearing test adapter to a web portal remote from the first patient site;
(d) transmitting a first access request from a first user at the first patient site to the web portal requesting a first hearing testing session;
(e) responsive to the first access request, receiving a first user interface at the first patient site from the web portal that is customized based on access permissions for the first user, wherein the access permissions permit the first user to provide hearing test feedback responsive to operation of the first hearing test adapter;
(f) receiving from the web portal an indication that a first test session has been created;
(g) receiving a first control operation associated with the first test session from the web portal;
(h) responsive to receiving the first control operation, transmitting a first operational command to the first hearing test adapter, wherein the first operational command changes an operation of the first hearing test adapter;
(i) responsive to the change in the operation of the first hearing test adapter, transmitting first test feedback from the first user to the web portal; and
further comprising the following steps at least some of which are carried out concurrently with steps (b) through (i):
receiving second device identification data uniquely identifying a second hearing test adapter at a second patient site from among the plurality of different patient sites;
transmitting the second device identification data from the second hearing test adapter to the web portal remote from the second patient site;
transmitting a second access request from a second user at the second patient site to the web portal requesting a second hearing testing session;
responsive to the second access request, receiving a second user interface at the second patient site from the web portal that is customized based on access permissions for the second user, wherein the access permissions permit the second user to provide hearing test feedback responsive to operation of the second hearing test adapter;
receiving from the web portal an indication that a second test session has been created;
receiving a second control operation associated with the second test session from the web portal;
responsive to receiving the second control operation, transmitting a second operational command to the second hearing test adapter, wherein the second operational command changes an operation of the second hearing test adapter; and
responsive to the change in the operation of the second hearing test adapter, transmitting second test feedback from the second user to the web portal.

14. The method of claim 13, wherein receiving the first device identification data uniquely identifying the first hearing test adapter comprises receiving the first device identification data from the first hearing test adapter coupled via an electronic interface between the first hearing test adapter and a first electronic device at the first patient site.

15. The method of claim 13 further comprising:
communicating with a microphone coupled to a first electronic device at the first patient site and/or coupled to the first hearing test adapter to receive measurements of environmental noise at the first patient site;
selecting an output device of a plurality of output devices to be coupled to the first hearing test adapter responsive to the received measurements of the environmental noise; and
prior to transmitting the first operational command to the first hearing test adapter, providing an electronic message to the first user indicating the output device to be coupled to the first hearing test adapter.

16. The method of claim 15 further comprising:
adjusting the first operational command transmitted to the first hearing test adapter responsive to the received measurements of the environmental noise.

17. The method of claim 13, wherein the first operational command changes the operation of the first hearing test adapter to alter an audio frequency of a tone transmitted into an ear of the first user.

18. The method of claim 13 further comprising inserting an in-ear test probe into an ear of the first user, wherein the first operational command changes the operation of the first hearing test adapter and/or the test probe to alter an internal pressure of the ear canal of the first user.

19. The method of claim 18, wherein altering the internal pressure of the ear canal of the first user comprises increasing a pressure of the internal pressure of the ear canal of the first user with respect to an atmospheric pressure including operating a manometer and/or a pump associated with the test probe.

20. The method of claim 13, further comprising providing a transducer that is configured to be inserted in or placed on an ear of the first user and a plurality of electrodes that are configured to be placed on the first user's face and/or head, wherein the first operational command changes the operation of the first hearing test adapter and/or the transducer to output a click, tone or speech sound using the transducer, the method further comprising transmitting, from the patient site to the web portal, data gathered from the electrodes that is in response to the click.

21. The method of claim 13 further comprising transmitting first multimedia communications to the web portal during the first test session, wherein transmitting multimedia communications comprises transmitting speech of the first user captured by a first electronic device at the first patient site and/or the first hearing test adapter during the first test session.

22. A medical hearing test system comprising:
a test probe configured to be inserted into an ear canal of a patient at a patient site;
a hearing test adapter configured to be communicatively coupled to the test probe and at the patient site, wherein the hearing test adapter comprises an integrated audiometer and a communication circuit configured to convert a control operation that is received from a network protocol into an operational command for the integrated audiometer and/or the test probe; and
a microphone coupled to the hearing test adapter and configured to receive measurements of environmental noise,
wherein the hearing test adapter is configured to perform operations comprising:
transmitting an access request requesting a hearing testing session from the hearing test adapter to a web portal over an electronic communications network between the hearing test adapter and the web portal;
responsive to the access request, receiving a user interface from the web portal that is customized based on access permissions for the patient, wherein the access permissions permit the patient to provide hearing test feedback responsive to operation of the hearing test adapter;
receiving the control operation for the integrated audiometer and/or the test probe from the web portal over the electronic communications network;
responsive to receiving the control operation, transmitting the operational command to the integrated audiometer and/or the test probe, wherein the operational command changes an operation of the integrated audiometer and/or the test probe;
receiving a response command from the integrated audiometer responsive to the operational command;
responsive to receiving the response command from the integrated audiometer, transmitting test feedback from the patient to the web portal over the electronic communications network,
communicating with the microphone to receive measurements of environmental noise at the patient site;
selecting the test probe from a plurality of output devices to be coupled to the hearing test adapter responsive to the received measurements of the environmental noise;
prior to transmitting the operational command to the integrated audiometer, providing an electronic message indicating the test probe to be coupled to the hearing test adapter; and
adjusting the operational command transmitted to the integrated audiometer responsive to the received measurements of the environmental noise.

23. The system of claim 22, wherein the hearing test adapter is configured to perform operations comprising:
receiving the control operation from the web portal over the electronic communications network;
translating the control operation to a data communication comprising the operational command for the test probe; and
electronically communicating the data communication to the test probe.

24. The system of claim 22, wherein the hearing test adapter is further configured to perform operations comprising:
transmitting the device identification data from the hearing test adapter to a web portal remote from the hearing test adapter.

25. The system of claim 22, wherein the operational command changes the operation of the integrated audiometer to alter an audio frequency of a tone transmitted by the test probe into the ear canal of the patient.

26. The system of claim 23, wherein the test probe comprises a manometer operatively associated with a pump, and wherein the operational command changes the operation of the test probe to alter an internal pressure of the ear canal of the patient using the manometer and/or the pump.

27. The system of claim 26, wherein altering the internal pressure of the ear canal of the patient comprises increasing the internal pressure of the ear canal of the patient with respect to an atmospheric pressure of the patient.

28. The method of claim 1, wherein the first hearing test adapter is a portable electronic device,
wherein a connection between the first integrated audiometer and the first hearing test adapter is a hardwired connection within the portable electronic device, and
wherein the first integrated audiometer comprises a tone generator configured to be controlled remotely so as to generate tone presentations that comply with hearing diagnostic standards.

29. The system of claim 22, wherein the hearing test adapter is a portable electronic device,
wherein a connection between the integrated audiometer and the hearing test adapter is a hardwired connection within the portable electronic device, and
wherein the integrated audiometer comprises a tone generator configured to be controlled remotely so as to generate tone presentations that comply with hearing diagnostic standards.

* * * * *